United States Patent
Nishide et al.

(10) Patent No.: US 7,313,216 B2
(45) Date of Patent: Dec. 25, 2007

(54) SCAN CONTROL METHOD AND X-RAY CT APPARATUS

(75) Inventors: Akihiko Nishide, Tokyo (JP); Kotoko Morikawa, Tokyo (JP); Akira Hagiwara, Tokyo (JP); Yasuhiro Imai, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/199,416

(22) Filed: Aug. 8, 2005

(65) Prior Publication Data

US 2006/0034419 A1 Feb. 16, 2006

(30) Foreign Application Priority Data

Aug. 13, 2004 (JP) .............................. 2004-235900

(51) Int. Cl.
*A61B 6/03* (2006.01)
(52) U.S. Cl. ............................................. 378/15; 378/4
(58) Field of Classification Search .................... 378/4, 378/8, 15, 20, 95
See application file for complete search history.

(56) References Cited

U.S. PATENT DOCUMENTS

| | | | | |
|---|---|---|---|---|
| 5,301,672 A | * | 4/1994 | Kalender | .................... 600/428 |
| 5,347,570 A | * | 9/1994 | Haaks | ..................... 378/98.12 |
| 5,412,562 A | * | 5/1995 | Nambu et al. | ................. 378/10 |
| 5,594,772 A | * | 1/1997 | Toki et al. | ..................... 378/20 |
| 5,684,855 A | | 11/1997 | Aradate et al. | |
| 5,864,598 A | | 1/1999 | Hsieh et al. | |
| 6,023,494 A | | 2/2000 | Senzig et al. | |
| 2003/0031290 A1 | | 2/2003 | Sugihara et al. | |
| 2003/0076920 A1 | | 4/2003 | Shinno et al. | |
| 2003/0123603 A1 | * | 7/2003 | Suzuki | ......................... 378/4 |

FOREIGN PATENT DOCUMENTS

| | | |
|---|---|---|
| JP | 2002-355242 | 12/2002 |
| JP | 2003-052684 | 2/2003 |
| JP | 2003-159244 | 6/2003 |
| JP | 2003-334188 | 11/2003 |
| JP | 2004-041674 | 2/2004 |
| JP | 2004-041675 | 2/2004 |
| JP | 2004-073360 | 3/2004 |

OTHER PUBLICATIONS

Xiaodong Xu et al.; "Collimator, X-Ray Irradiator, and X-Ray Apparatus"; U.S. Appl. No. 10/982,114, filed Nov. 4, 2004; 14 pgs.

* cited by examiner

*Primary Examiner*—Chih-Cheng Glen Kao
(74) *Attorney, Agent, or Firm*—Armstrong Teasdale LLP

(57) ABSTRACT

A scan control method for an X-ray CT apparatus wherein a subject with a contrast agent injected therein is helically scanned with an X-ray beam and image reconstruction is performed based on projection data obtained through an X-ray detector. The method includes controlling a velocity of a helical scan following motion of the contrast agent in the subject.

20 Claims, 25 Drawing Sheets

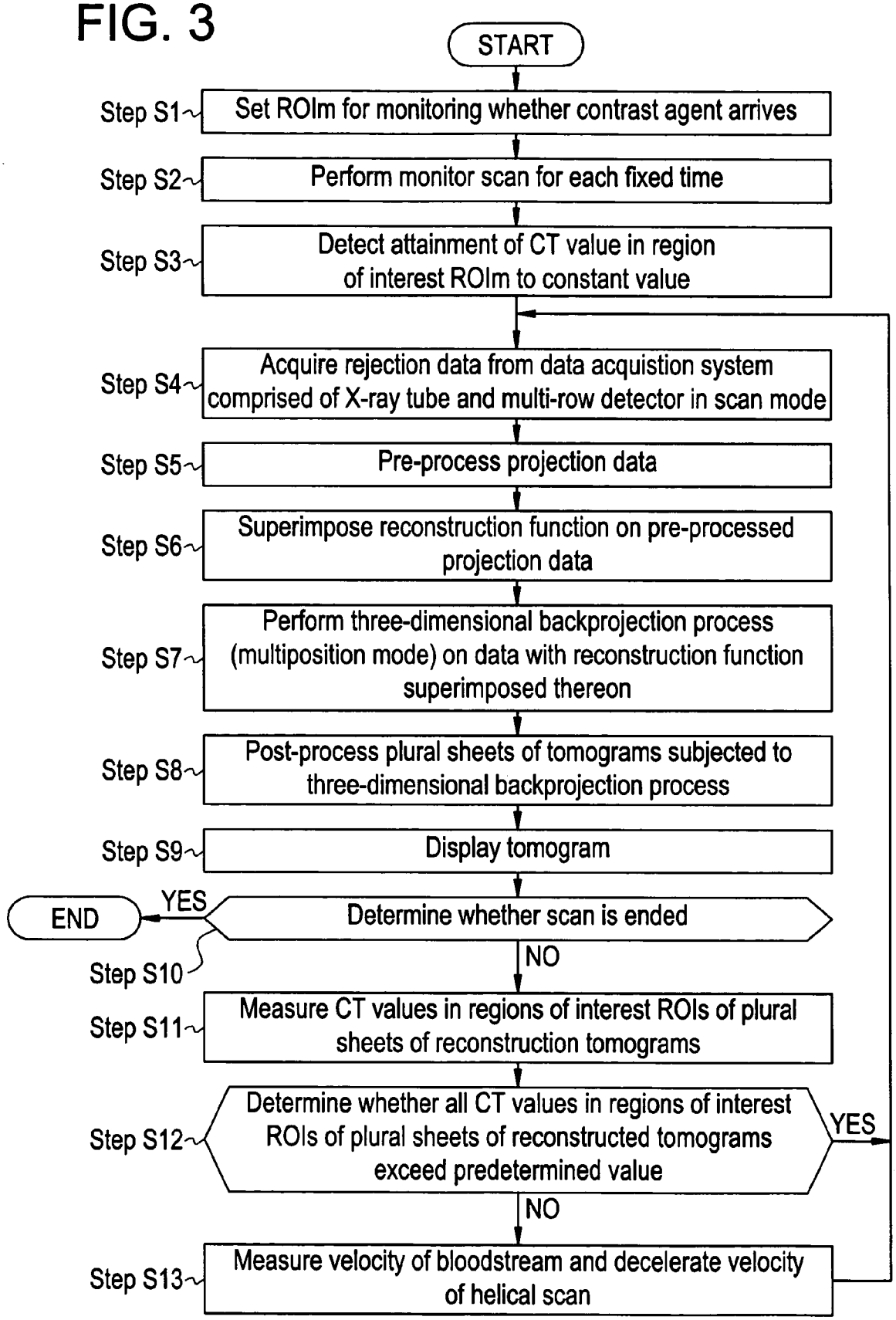

Monitoring phase

Time t

Δtm

Region of interest ROIm

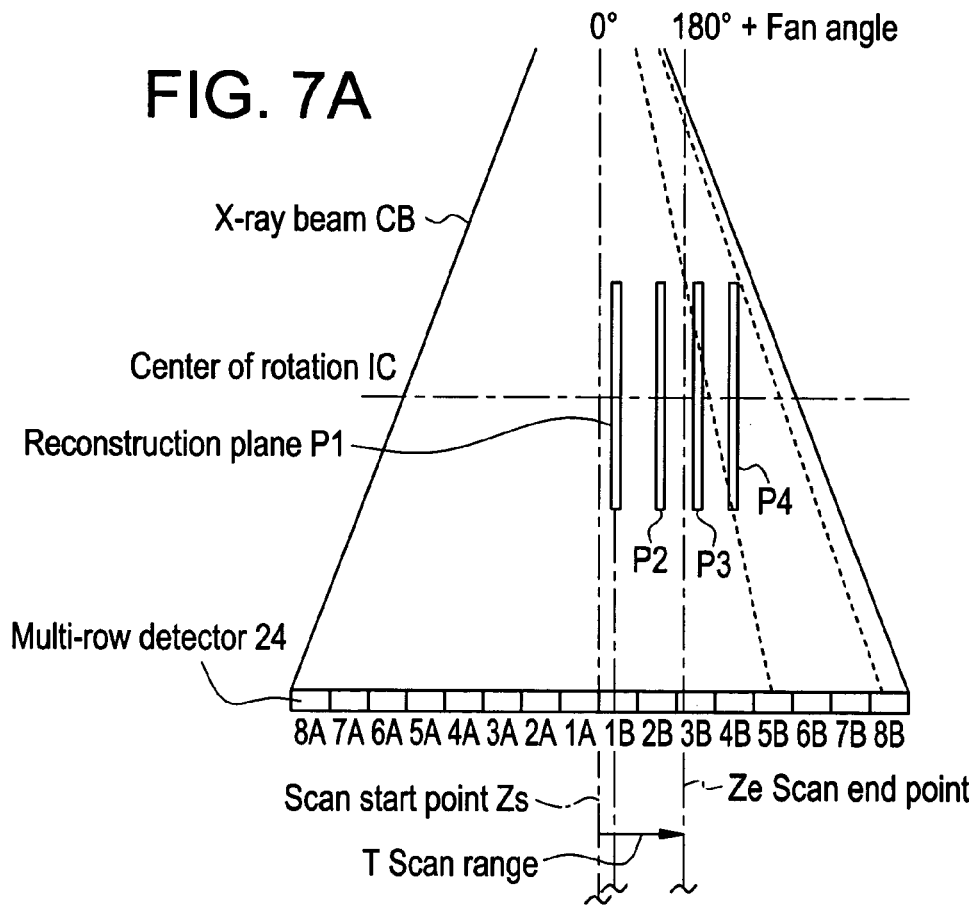
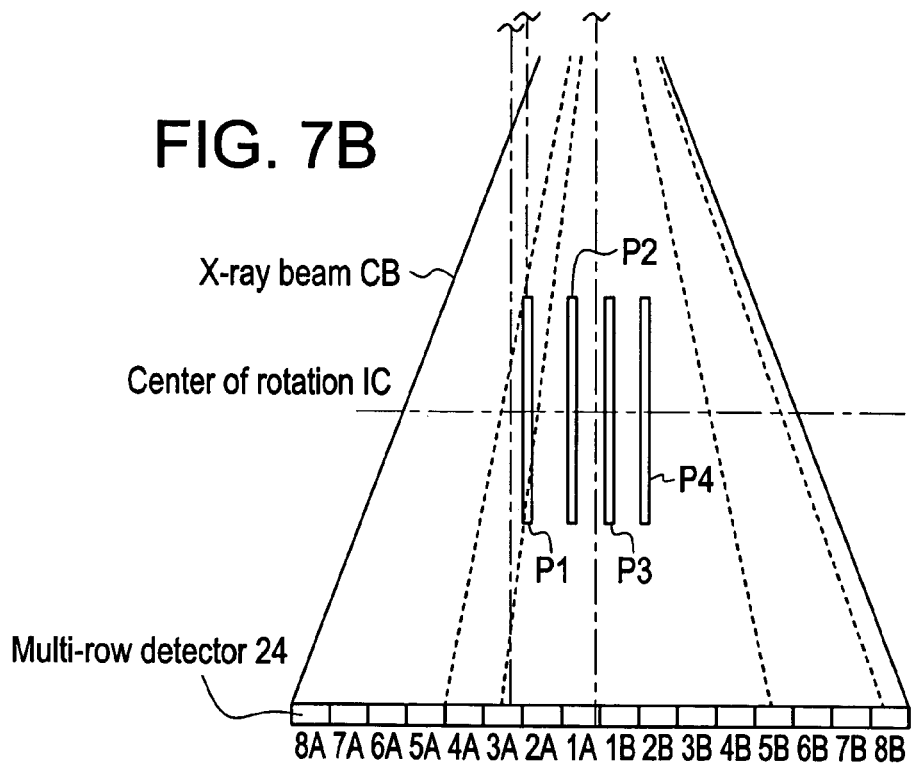

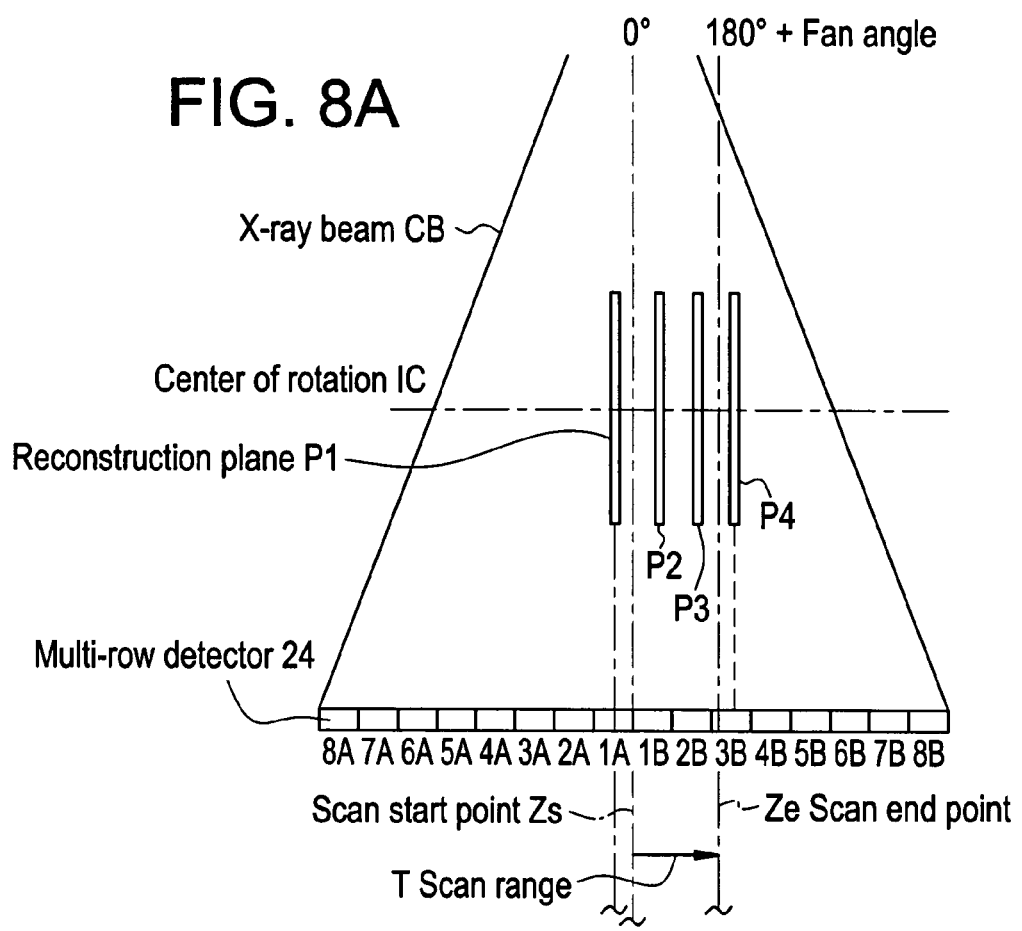
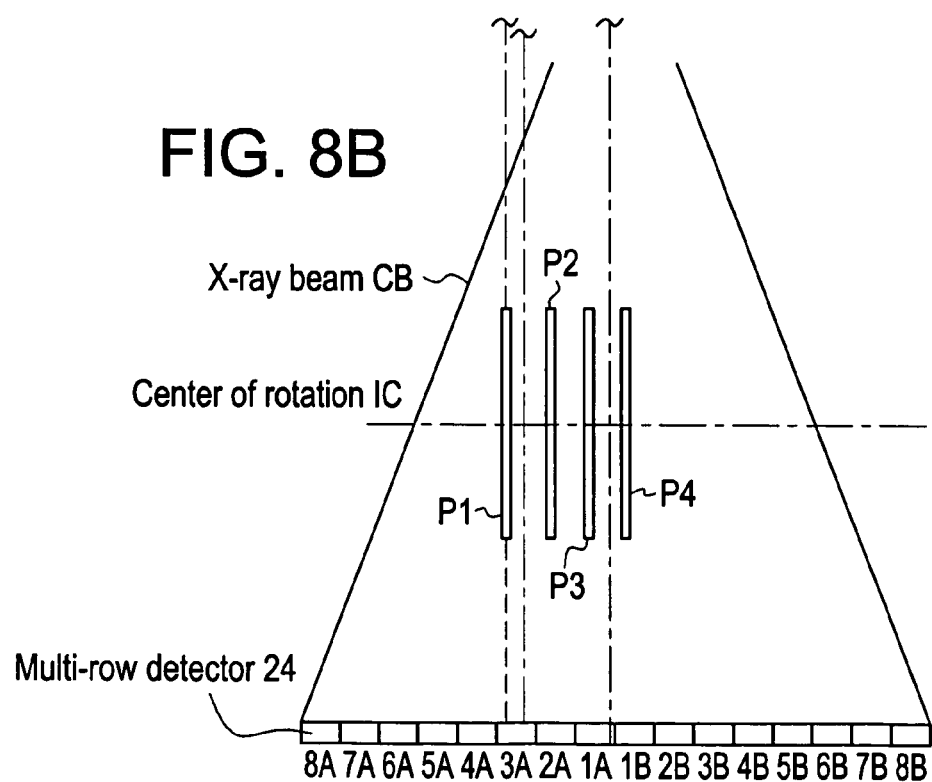

Dr (0°, x, y)

D2 (0°, x, y)

Region of interest
ROIsn ($x_{sn}$, $y_{sn}$, $l_{xn}$, $l_{yn}$)

Slice n
Slice n+1
Slice n+2
Slice n+3 z

Region of interest
Start point of ROIsi ($x_{si}$, $y_{si}$)

$ly_i$ $lx_i$

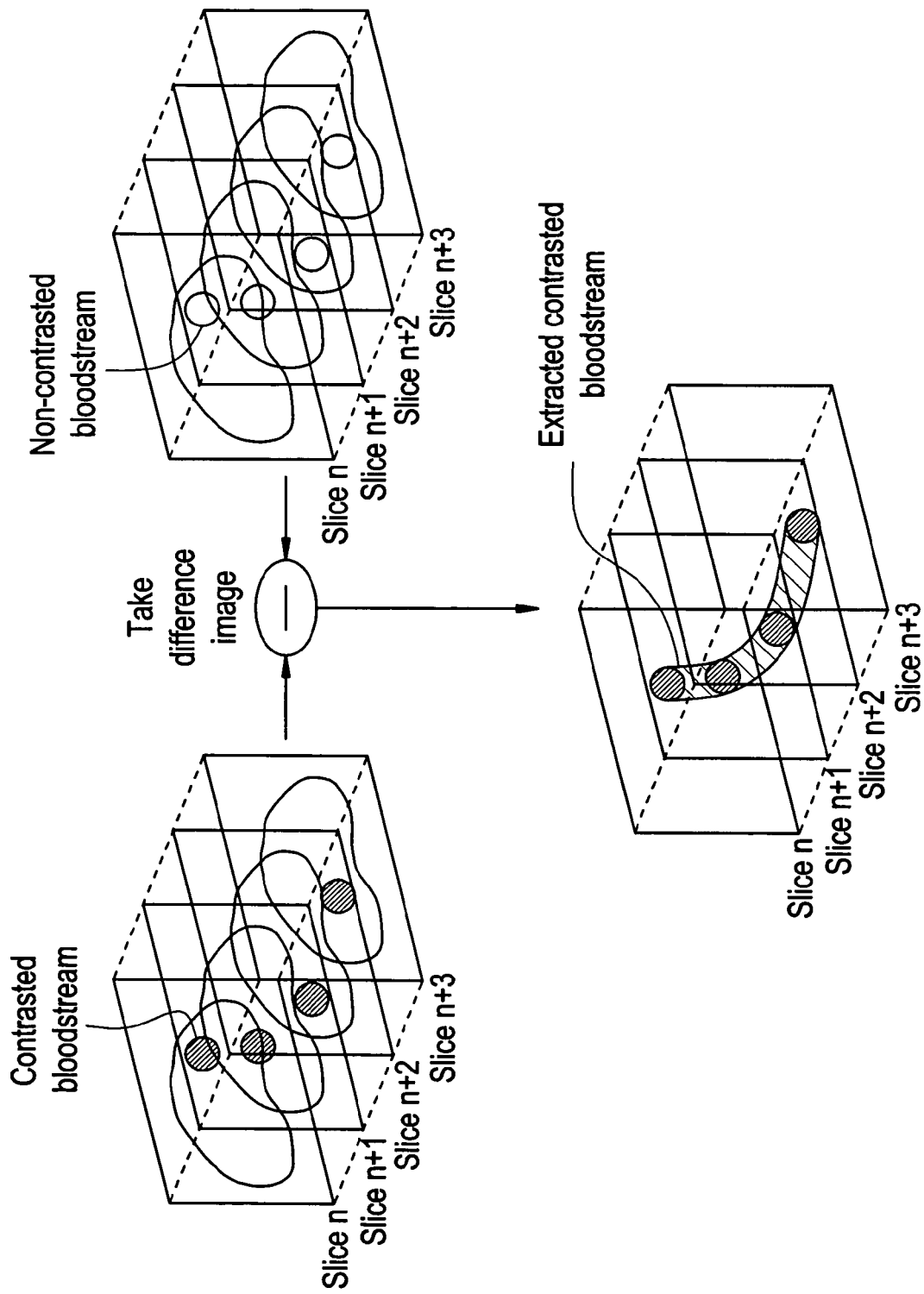

SCAN CONTROL METHOD AND X-RAY CT APPARATUS

CROSS REFERENCE TO RELATED APPLICATIONS

This Application claims the benefit of Japanese Application No. 2004-235900 filed Aug. 13, 2004.

BACKGROUND OF THE INVENTION

The present invention relates to a scan control method and an X-ray CT (Computed Tomography) apparatus, and more specifically to a scan control method for an X-ray CT apparatus, for helically scanning a subject with a contrast agent injected therein, and an X-ray CT apparatus which helically scans a subject with a contrast agent injected therein. Alternatively, the present invention relates to an applied technology for a variable helical scan in an X-ray CT apparatus.

In an X-ray CT apparatus which helically scans a subject with a contrast agent injected therein, a helical scan is performed which is synchronized with the attainment of a bloodstream contrasted with a contrast agent to a region of interest in a monitor phase. In such a case, a scan with a helical scan velocity as constant is carried out after the start of the helical scan (refer to, for example, the following patent document 1).

[Patent Document 1] Japanese Unexamined Patent Publication No. Hei 09(1997)-327454 (fourth to fifth pages and FIGS. 7 through 9).

In order to suitably perform contrast photography by the scan with the helical scan velocity as constant, there is a need to make a bloodstream contrasted with a contrast agent in advance. Therefore, the contrast agent is apt to often use so that a burden on a patient increases. With this view, there is a need to reduce the amount of the contrast agent as much as possible.

In an X-ray CT apparatus which makes use of a multi-row X-ray detector or a plane X-ray detector, the velocity of a helical scan is on the increase with an increase in helical pitch due to three-dimensional image reconstruction and enlargement of a detector width in a z-axis (body-axis) direction. The velocity of the helical scan might be faster than the velocity of the bloodstream contrasted with the contrast agent. Therefore, there has been a demand for control of the helical scan velocity.

SUMMARY OF THE INVENTION

Therefore, an object of the present invention is to realize a scan control method for performing the optimum contrast photography by an X-ray CT apparatus, and an X-ray CT apparatus which carries out the optimum contrast photography.

Another object of the present invention is to realize a scan control method for an X-ray CT apparatus, for bringing only a contrasted part into image form, and an X-ray CT apparatus which images only a contrasted part.

(1) The invention according to one aspect for attaining the above objects provides a scan control method for an X-ray CT apparatus wherein a subject with a contrast agent injected therein is helically scanned with an X-ray beam and image reconstruction is performed based on projection data obtained through an X-ray detector, which comprises controlling a velocity of a helical scan following motion of the contrast agent in the subject.

(2) The invention according to another aspect for attaining the above objects provides an X-ray CT apparatus comprising an X-ray source, an X-ray detector disposed so as to be opposed to the X-ray source with a subject with a contrast agent injected therein being interposed therebetween, image reconstructing means for helically scanning the subject and reconstructing an image on the basis of projection data obtained through the X-ray detector, and control means for controlling a helical scan, wherein the control means controls the velocity of the helical scan following motion of the contrast agent in the subject.

The X-ray detector is preferably a multi-row X-ray detector, a matrix-form X-ray detector or a plane matrix-form X-ray detector in that an efficient scan is performed using a cone beam X-ray.

A moving velocity of the contrast agent is preferably estimated on the basis of a position of a tomogram at which the head of the contrast agent has arrived, of a plurality of tomograms reconstructed by a three-dimensional back-projection process and different in position as viewed in the direction of progress of the helical scan in that the velocity of the helical scan is suitably controlled.

The tomogram at which the head of the contrast agent has arrived, is preferably detected based on each of CT values of predetermined regions of interest in that the position of the tomogram at which the head of the contrast agent has arrived, is suitably detected.

The regions of interest are preferably set independently every individual tomograms of the plurality of tomograms in that the tomogram at which the head of the contrast agent has arrived, is suitably detected.

The velocity of the helical scan is preferably changed continuously halfway through the scan in that contrast photography is suitably performed.

Intervals among the plurality of tomograms as viewed in the progress direction of the helical scan are preferably constant in that the velocity of the contrast agent is suitably detected. The intervals among the plurality of tomograms as viewed in the progress direction of the helical scan may preferably be indefinite intervals.

A monitoring scan for detecting a change in the CT value of each of the regions of interest is preferably performed prior to the start of the helical scan in that the first attainment of the contrast agent to the corresponding region of interest is detected.

In the invention according to each of the respective aspects referred to above, the velocity of a helical scan is controlled following motion of a contrast agent in a subject. It is therefore possible to realize a scan control method for performing the optimum contrast photography by an X-ray CT apparatus, and an X-ray CT apparatus which carries out the optimum contrast photography.

A helical scan is controlled in such a manner that the position of center of the X-ray detector as viewed in the progress direction of the helical scan is equivalent to the position of a leading end of a contrast agent. Images are reconstructed on the basis of projection data respectively obtained through a first half and a latter half as viewed in the progress direction of the helical scan with respect to the center position of the X-ray detector, and thereby an image corresponding to a difference between the images is obtained. It is therefore possible to realize a scan control method for an X-ray CT apparatus, for imaging only a contrasted part, and an X-ray CT apparatus which brings only a contrasted part into image form.

Further objects and advantages of the present invention will be apparent from the following description of the preferred embodiments of the invention as illustrated in the accompanying drawings.

BRIEF DESCRIPTION OF THE DRAWINGS

FIG. 3 is a flow diagram showing a schematic operation of the X-ray CT apparatus according to one embodiment of the present invention.

FIGS. 7a and 7b are explanatory diagrams depicting image reconstruction positions.

FIGS. 8a and 8b are explanatory diagrams showing image reconstruction positions.

FIG. 30 is an explanatory diagram showing the manner in which only a contrasted bloodstream is extracted from images corresponding to differences, at the same regions and locations, among tomograms of contrasted bloodstreams and tomograms of non-contrasted bloodstreams in the embodiment 2.

DETAILED DESCRIPTION OF THE INVENTION

Figure 1:
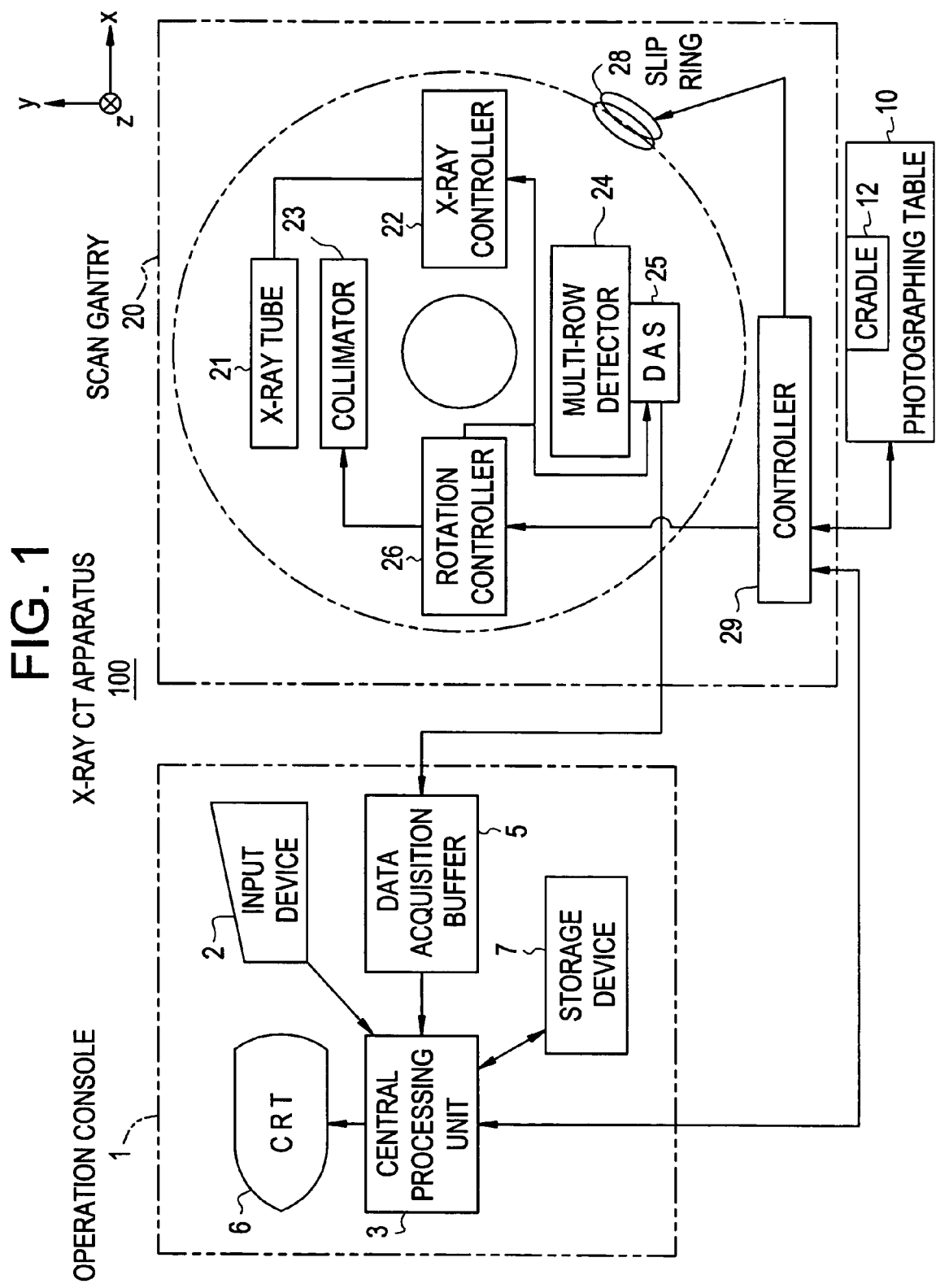
FIG. 1 is a block diagram showing an X-ray CT apparatus illustrative of one example of the best mode for carrying out the present invention.

Best modes for carrying out the invention will be explained below with reference to the accompanying drawings. Incidentally, the present invention is not limited to the best modes for carrying out the invention. A block diagram of an X-ray CT apparatus is shown in FIG. 1. The present apparatus is one example showing the best mode for carrying out the present invention. One example of the best mode for carrying out the present invention related to the X-ray CT apparatus is shown by the configuration of the present apparatus. One example of the best mode for carrying out the present invention related to a scan control method is shown by the operation of the present apparatus.

The X-ray CT apparatus 100 is equipped with an operation console 1, a photographing table 10 and a scan gantry 20. The operation console 1 is equipped with an input device 2 which accepts an input from an operator, a central processing unit 3 which executes an image reconstructing process or the like, a data acquisition buffer 5 which acquires or collects projection data acquired by the scan gantry 20, a CRT 6 which displays a CT image reconstructed from the projection data, and a storage device 7 which stores programs, data and X-ray CT images therein. The central processing unit 3 is one example of an image reconstructing means according to the present invention.

The table device 10 is provided with a cradle 12 which inserts and draws a subject into and from a bore (cavity portion) of the scan gantry 20 with the subject placed thereon. The cradle 12 is elevated and moved linearly along the table by a motor built in the photographing table 10. Coordinates in a z-axis direction are counted by an encoder. The corresponding z-axis coordinate is calculated by a controller 29. The controller 29 adds a z-axis coordinate Z (view, i) of the photographing table to its corresponding projection data D0 (view, j, i) of a DAS through a slip ring 28. Here, a channel number, a detector row or sequence and a view angle are assumed to be i, j and view respectively.

The scan gantry 20 is equipped with an X-ray tube 21, an X-ray controller 22, a collimator 23, a multi-row detector 24, the DAS (Data Acquisition System) 25, a rotation controller 26 which rotates the X-ray tube 21 or the like about a body axis of the subject and controls the collimator 23, and the controller 29 which performs the transfer of control signals or the like between the operation console 1 and the photographing table 10.

The X-ray tube 21 is one example of an X-ray source according to the present invention. The multi-row detector 24 is one example of an X-ray detector according to the present invention. The controller 29 is one example of a control means according to the present invention.

Figure 2:
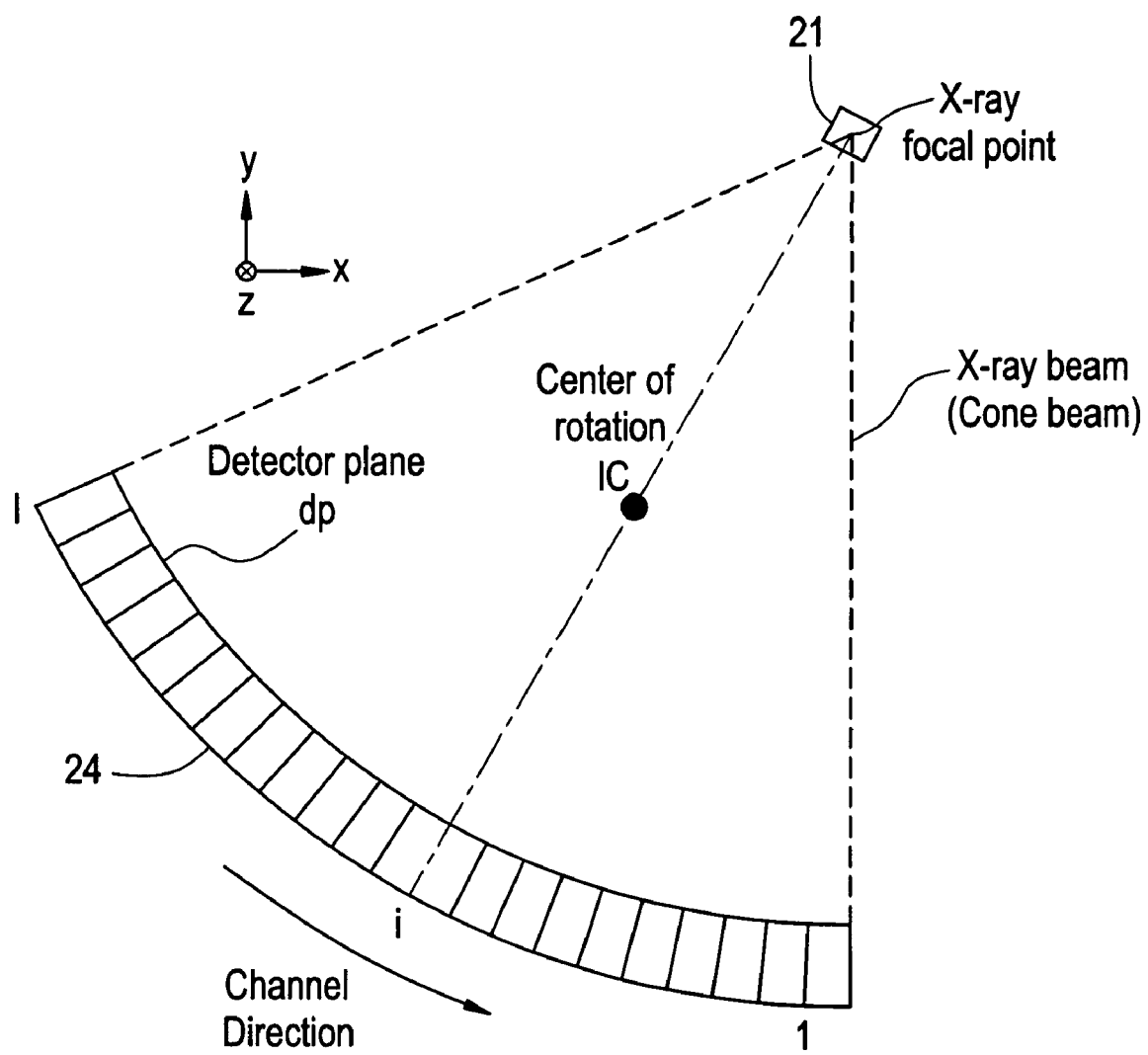
FIG. 2 is an explanatory diagram illustrating rotation of an X-ray tube and a multi-row detector.

FIG. 2 is an explanatory view showing the X-ray tube 21 and the multi-row detector 24. The X-ray tube 21 and the multi-row detector 24 rotate about the center of rotation IC. When the vertical direction is assumed to be a y direction, the horizontal direction is assumed to be an x direction and the direction orthogonal to these is assumed to be a z direction, the plane of rotation of each of the X-ray tube 21 and the multi-row detector 24 is an xy plane. The direction of movement of the cradle 12 corresponds to the z direction.

An X-ray beam called cone beam CB is generated by the X-ray tube 21 and the collimator 23. When the direction of a center axis of the cone beam CB is parallel to the y direction, the view angle is assumed to be equal to 0°. The multi-row detector 24 has detector rows corresponding to 256 rows, for example. The direction of side-by-side provision of the detector rows corresponds to the z direction. The respective detector rows respectively have channels corresponding to 1024 channels, for example.

The operation of the present apparatus will be explained. FIG. 3 is a flow diagram schematically showing the operation of an embodiment 1 illustrative of the X-ray CT apparatus 100.

In Step S1, a region of interest for monitoring whether a contrast agent arrives, is set. Consequently, such a region of interest ROIm as shown in FIG. 4(b), for example, is set.

In Step S2, a monitor scan is performed for each fixed time.

Figure 4A:
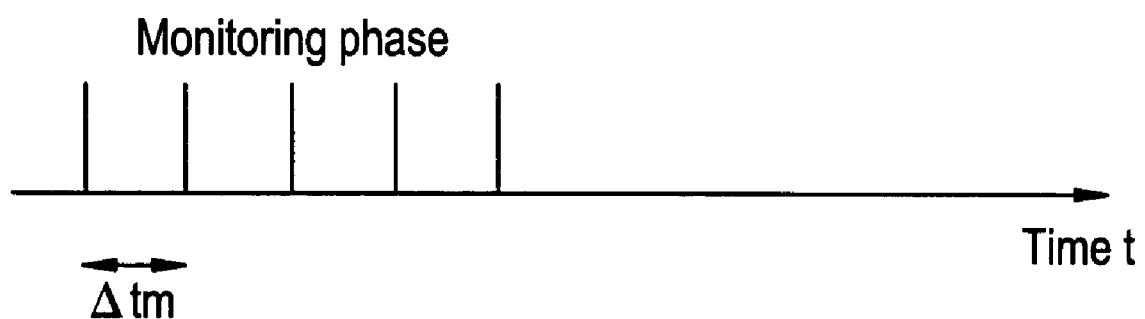
FIGS. 4a and 4b are explanatory diagrams depicting a monitoring phase.
Figure 4B:
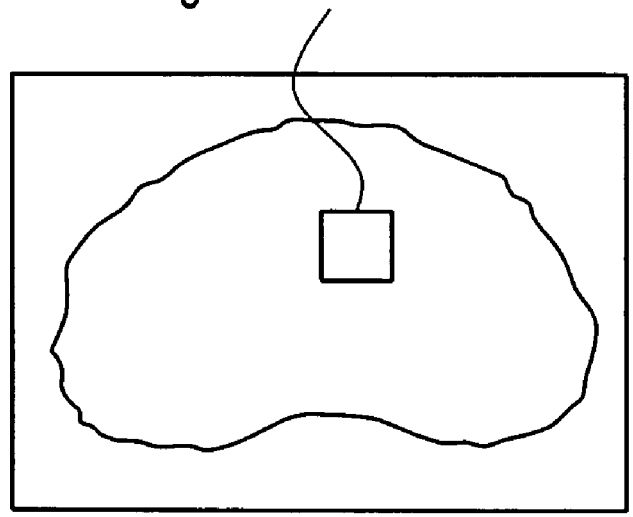

In a monitor phase, the present apparatus performs a conventional scan (axial scan) for each predetermined cycle Δtm as shown in FIG. 4(a) and waits for an average CT value in the region of interest ROIm to reach a constant value or more. It is found that the contrast agent arrives when the average CT value has exceeded a threshold value. The conventional scan at this time may be a single scan or multiscans.

In Step S3, the attainment of the CT value in the ROI to the constant value is detected.

In Step S4, projection data are acquired or collected from the data acquisition system comprised of the X-ray tube and multi-row detector in a scan mode. A table linear movement position z and projection data D (view, j, i) expressed in the view angle, detector row number j and channel number i are acquired while the X-ray tube 21 and the multi-row detector 24 are being rotated about a subject to be photographed and the cradle 12 is being linearly moved along the table. That is, the acquisition of data by a helical scan is performed. Incidentally, at this time, z-coordinate information Z (view) of the photographing table at the center position in the z direction, of the data acquisition system comprised of the multi-row detector 24 and the X-ray tube 21 is added to the projection data as z coordinates of the photographing table in the z-axis direction. This data acquisition process will be described later with reference to FIGS. 5 through 9.

Figure 5A:
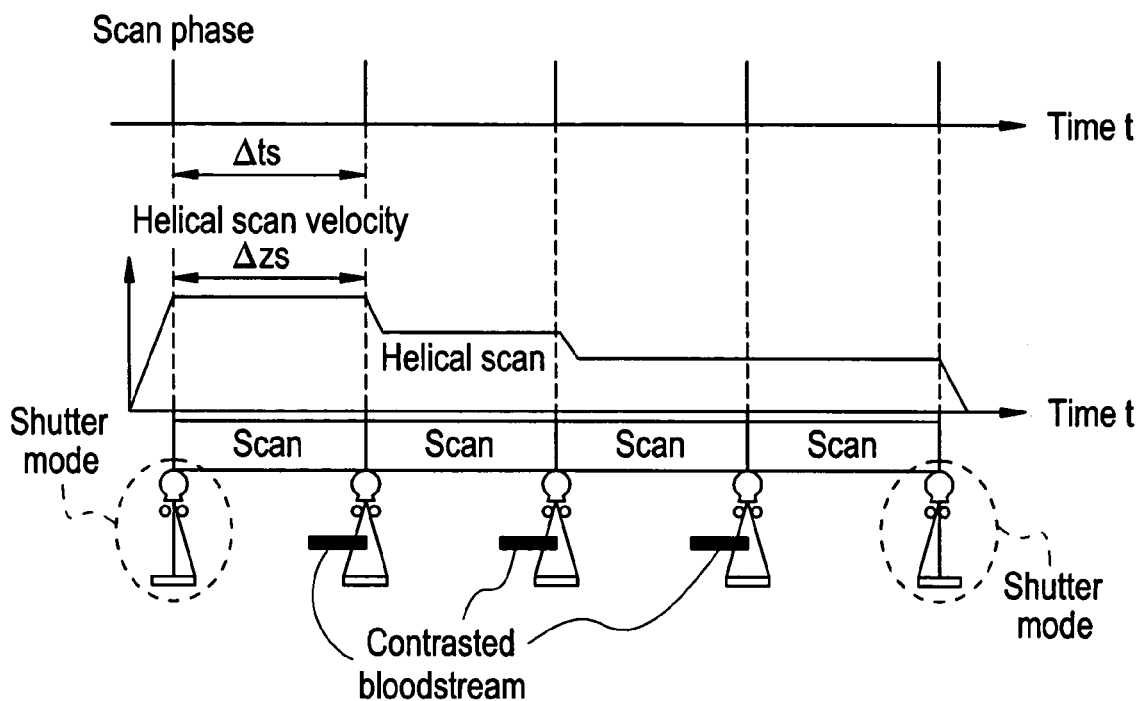
FIGS. 5a and 5b are explanatory diagrams showing a scan phase.
Figure 5B:
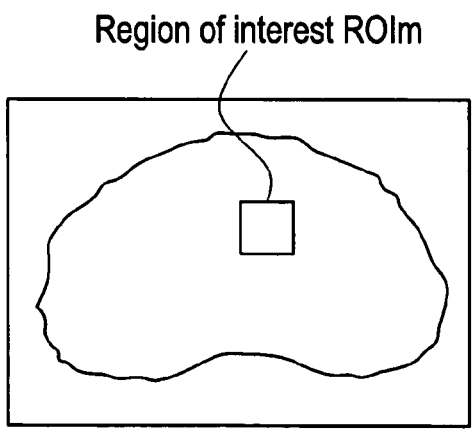

In a scan phase as shown in FIG. 5(a), image reconstruction based a variable pitch helical scan (variable pitchscan) is performed at predetermined cycles Δts. The cycle of the image reconstruction may not be identical to a cycle corresponding to one rotation of a scan. In this image reconstruction, a plurality of sheets of tomograms are reconstructed in a multiposition mode to be described later. The position of the contrast agent is judged depending on whether the average CT value in the region of interest ROIs exceeds the threshold value up to tomograms of any positions. Incidentally, x and y coordinate positions of the region of interest ROIs set as shown in FIG. 5(b) may be caused to depend on positions in the z-axis direction.

Figure 6:
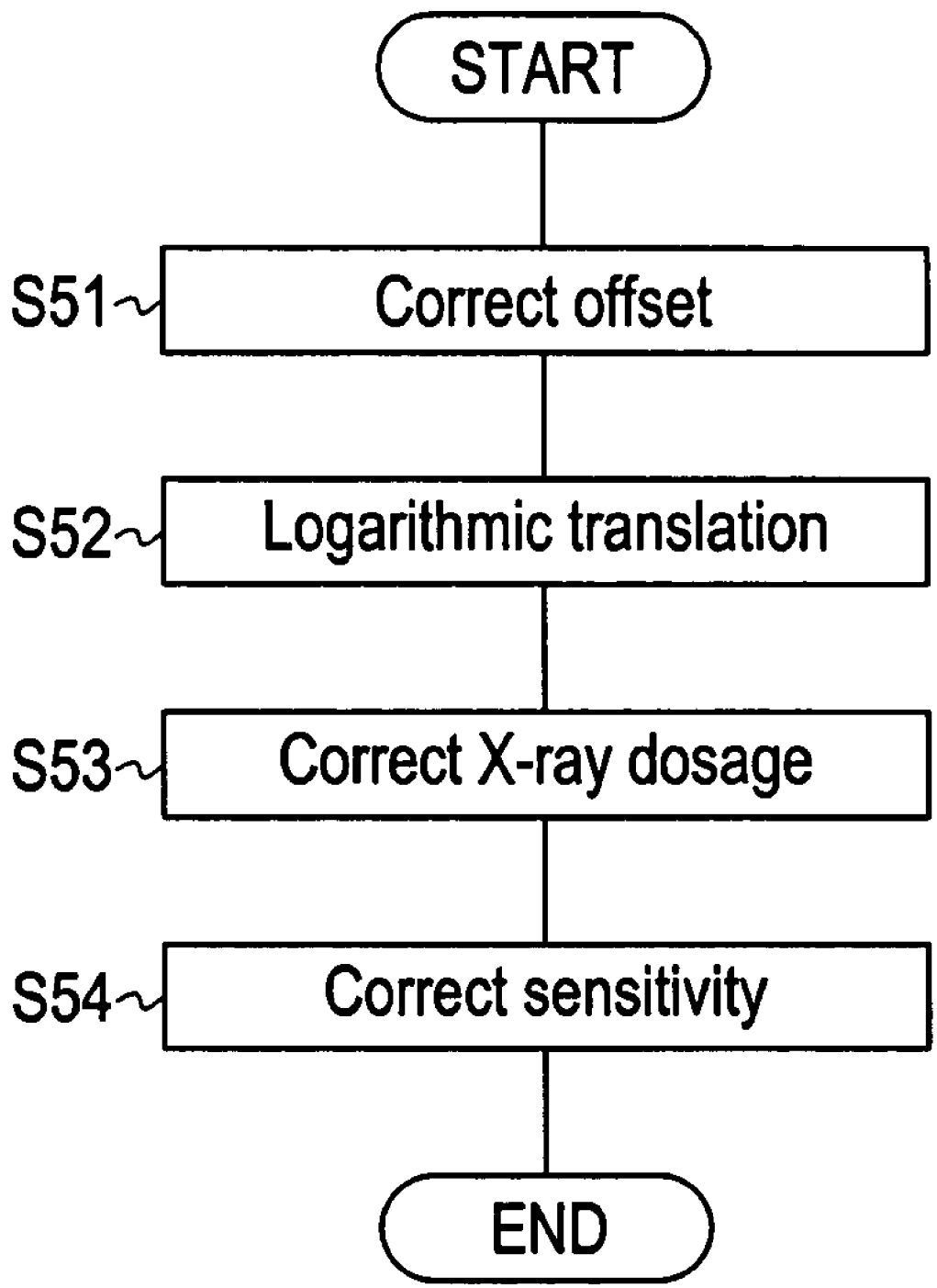
FIG. 6 is a flow diagram illustrating a schematic operation of the X-ray CT apparatus according to the one embodiment of the present invention.

In Step S5, as indicated in Step S5 of FIG. 3, pre-processing (offset correction (Step S51)), logarithmic translation (Step S52), X-ray dosage correction (Step S53) and sensitivity correction (Step S54) is effected on the projection data D0 (view, j, i) as shown in a flow diagram of FIG. 6.

In Step S6, a reconstruction function superimposition process is effected on the pre-processed projection data D0 (view, j, i). That is, the projection data is Fourier-transformed and multiplied by a reconstruction function, followed by being inversely Fourier-transformed.

In Step S7, a three-dimensional backprojection process (multiposition mode) is performed on the projection data D0 (view, j, i) subjected to the reconstruction function superimposition process to determine backprojection data D3 (x, y). The three-dimensional backprojection process will be described later with reference to FIG. 21.

Incidentally, the multiposition mode is equivalent to a mode in which the time phases of a plurality of CT images can be provided. Data are acquired by the conventional scan (axial scan) or helical scan using the multi-row detector, and a plurality of tomograms different in slice position can be generated from data acquired by one axial scan or one rotational helical scan.

Only one sheet of tomogram indicated by P1 could be reconstructed in the helical scan as shown in FIG. 7 in the prior art. Even in the case of the axial scan, image reconstruction could be performed only at row center positions of multi-row detectors 8A, 7A, 6A, 5A, 4A, 3A, 2A, 1A, 1B, 2B, 3B, 4B, 5B, 6B, 7B and 8B as shown in FIG. 8 in the prior art.

In the multiposition mode using three-dimensional image reconstruction, however, tomograms of P1 through P4 (or much more) can be three-dimensionally image-reconstructed in the helical scan as shown in FIG. 8. Even in the case of the axial scan, the tomograms can be three-dimensionally image-reconstructed at free positions even at other than the row center positions of the multi-row detectors.

It can be judged by the multiposition mode that if an average CT value is higher than a threshold value for determining whether a predetermined contrasted bloodstream arrives, within a region of interest ROIs of each of the tomograms subjected to the three-dimensional image reconstruction, then the contrasted bloodstream has arrived.

Figure 9:
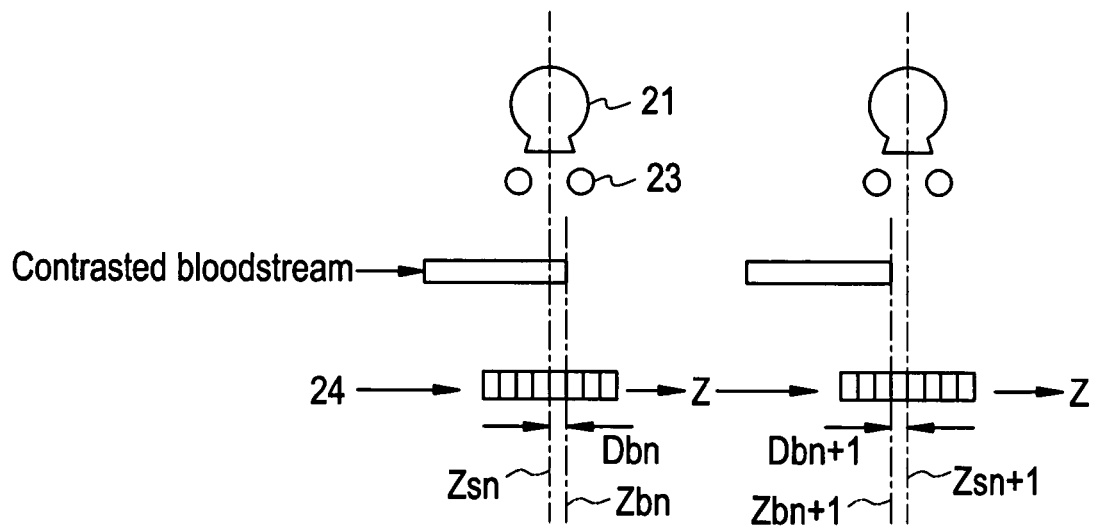
FIG. 9 is an explanatory diagram illustrating helical scan velocity control.

That is, as shown in FIG. 9, if a decision can be made about to which slice the most leading edge of the contrasted bloodstream exists, then the velocity of a bloodstream contrasted in accordance with its time is recognized. A distance $D_{bn}$ extending from the center coordinate of the data acquisition system is recognized. That is, if the most leading edge of a bloodstream contrasted in an nth slice as viewed from the center exists (where n: 1 origin), then a z coordinate $Z_{bn}$ of the most leading edge of the contrasted bloodstream and the center coordinate $Z_{sn}$ of the data acquisition system are expressed in the following relation:

$$Z_{bn}=Z_{sn}+D_{bn} \quad (1)$$

Therefore, a velocity adjustment amount $\Delta V_{hn}$ for variable pitch helical is expressed in the following manner:

$$\Delta V_{hn} = \frac{Z_{bn+1} - Z_{bn}}{t_{n+1} - t_n} - V_{hn} \quad (2)$$

$$= \frac{(Z_{sn+1} + D_{bn+1}) - (Z_{sn} + D_{bn})}{t_{n+1} - t_n} - V_{hn}$$

In Step S8, the backprojection data D3 (x, y) is post-processed to obtain a CT image.

Figure 10:
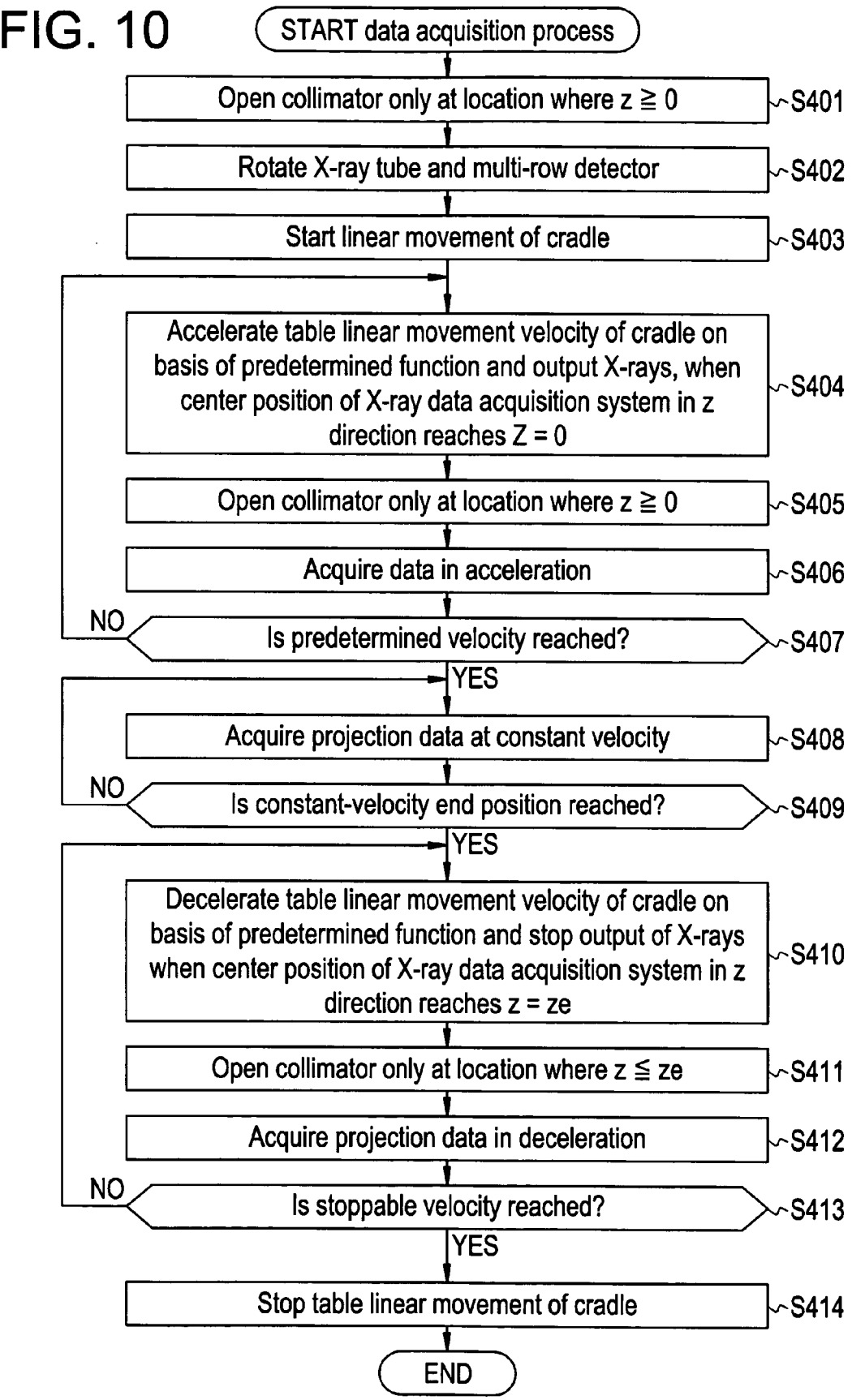
FIG. 10 is a flow diagram showing the details of a data acquisition process.

FIG. 10 is a flow diagram showing the details of the data acquisition process (Step S4 in FIG. 3).

In Step S401, the collimator is kept open only at a location where $z \geqq 0$.

In Step S402, the X-ray tube 21 and the multi-row detector 24 are rotated about a subject to be photographed.

In Step S403, the table linear movement of the cradle 12 is started.

Figure 11:
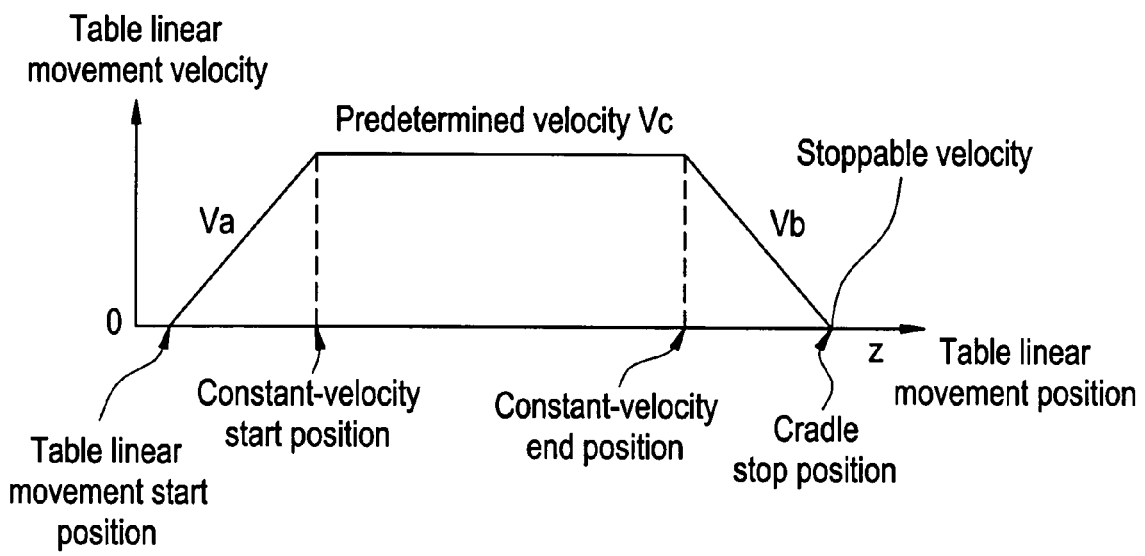
FIG. 11 is a graph showing a change in table linear movement velocity where acceleration and deceleration are linearly performed.
Figure 12:
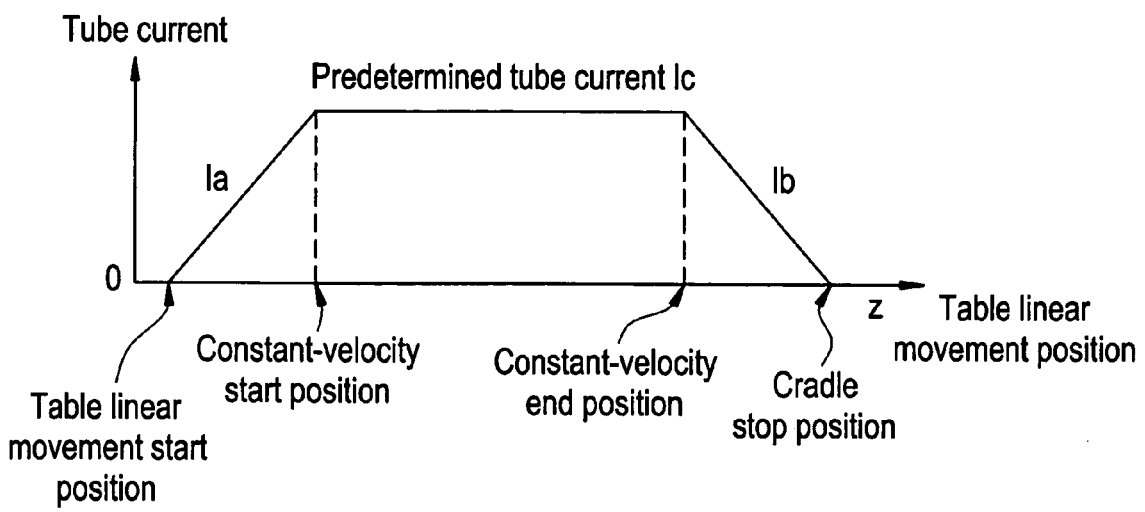
FIG. 12 is a graph depicting a change in tube current where acceleration and deceleration are linearly performed.
Figure 13:
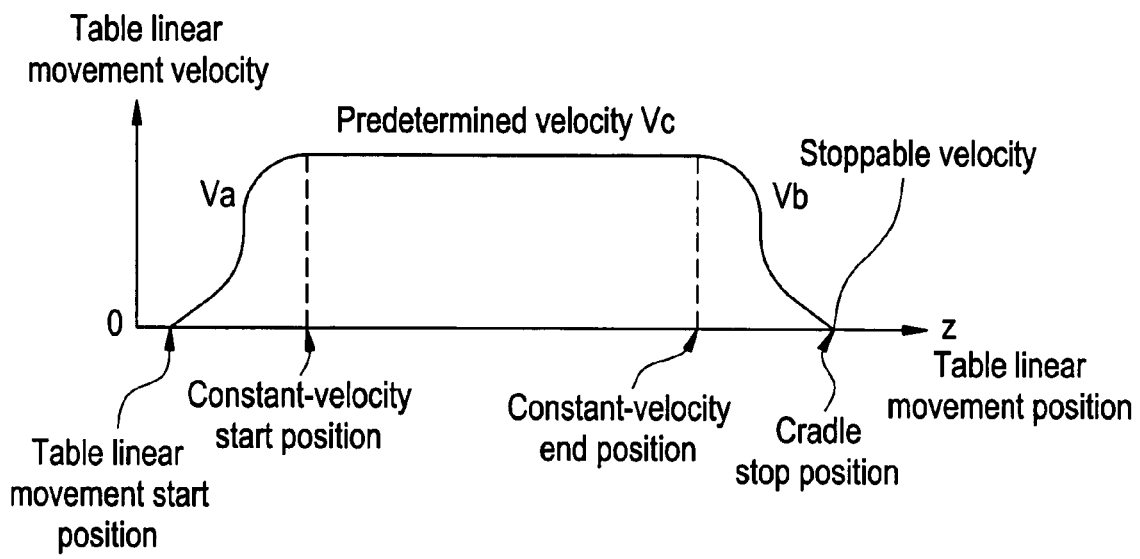
FIG. 13 is a graph showing a change in table linear movement velocity where acceleration and deceleration are nonlinearly performed.
Figure 14:
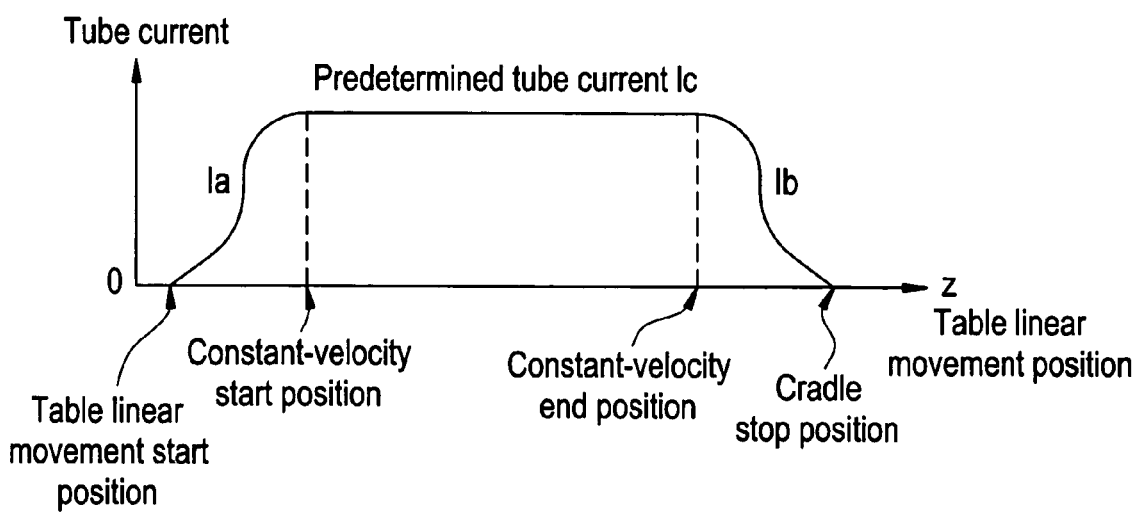
FIG. 14 is a graph illustrating a change in tube current where acceleration and deceleration are nonlinearly performed.

In Step S404, the velocity of the table linear movement of the cradle 12 is accelerated on the basis of a predetermined function. A tube current is increased in such a manner that the velocity and tube current become a constant value in accordance with its acceleration. A case in which the predetermined function is linear relative to the time, is shown in FIGS. 11 and 12, and a case in which the predetermined function is nonlinear relative to the time, is shown in FIGS. 13 and 14. When the position of center of the X-ray data acquisition system in the z direction reaches z=0, X rays are outputted. Further, opening/closing control of the collimator is also performed.

Assuming that the degree of opening of the collimator at this time is represented as follows:

cw: collimator opening/closing width,
zce: z coordinate maximum value of collimator opening/closing (+side), and
zcs: z coordinate minimum value of collimator opening/closing (–side),
cw=zce–zcs is reached.

Assuming that zd, zs and ze are represented as follows:
zd: center z coordinate of data acquisition system,
zs: z coordinate at the start of helical scan (zs=0), and
ze: z coordinate at the stop of helical scan,
zce is controlled so as to take zcs=zs=0 at the start of X-ray data acquisition at this time. Upon the completion of the X-ray data acquisition, zce is controlled so as to reach the z-coordinate+side of a set slice thickness and zcs=ze.

Figure 15:
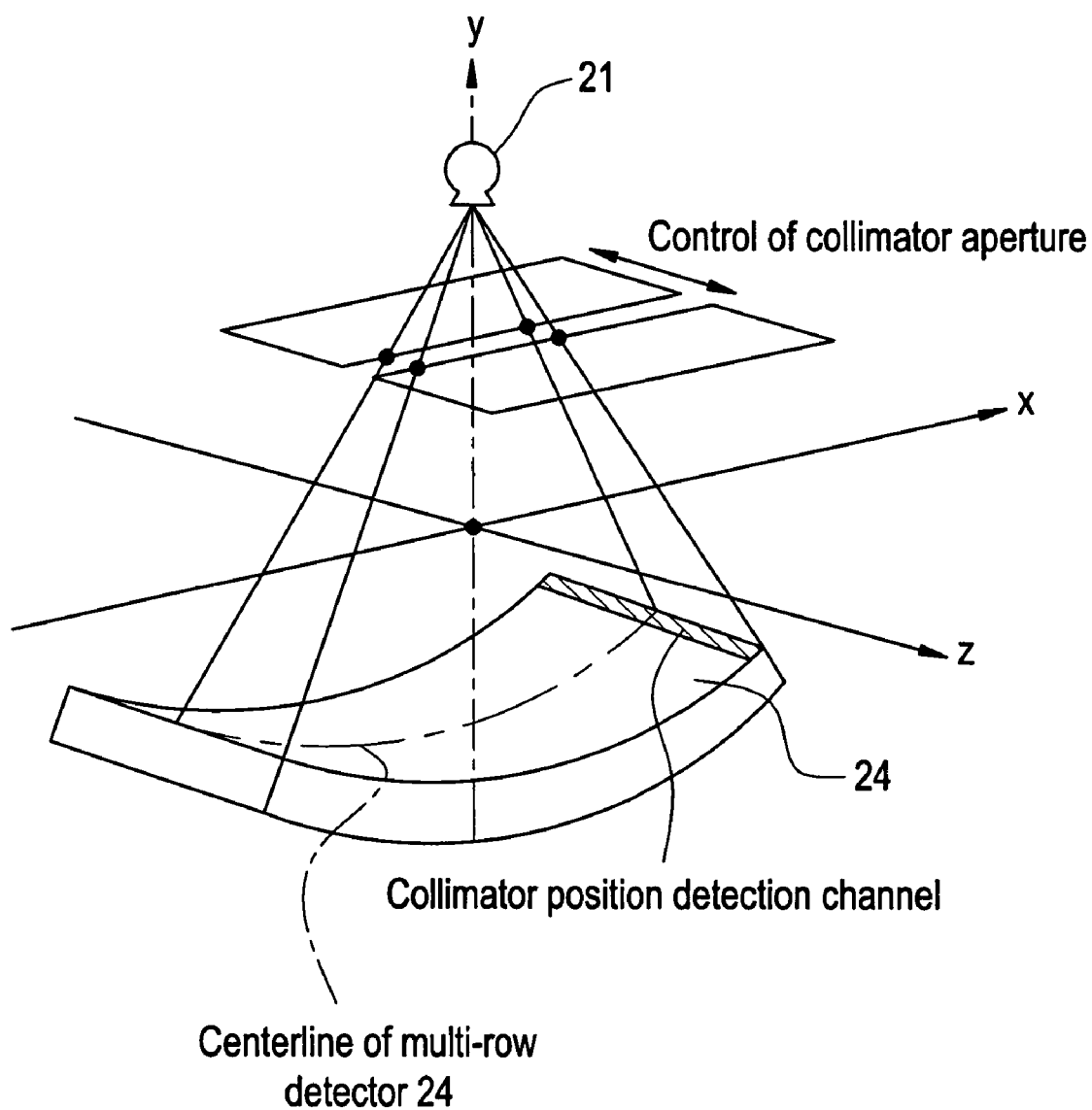
FIG. 15 is a diagram showing collimator control.
Figure 16:
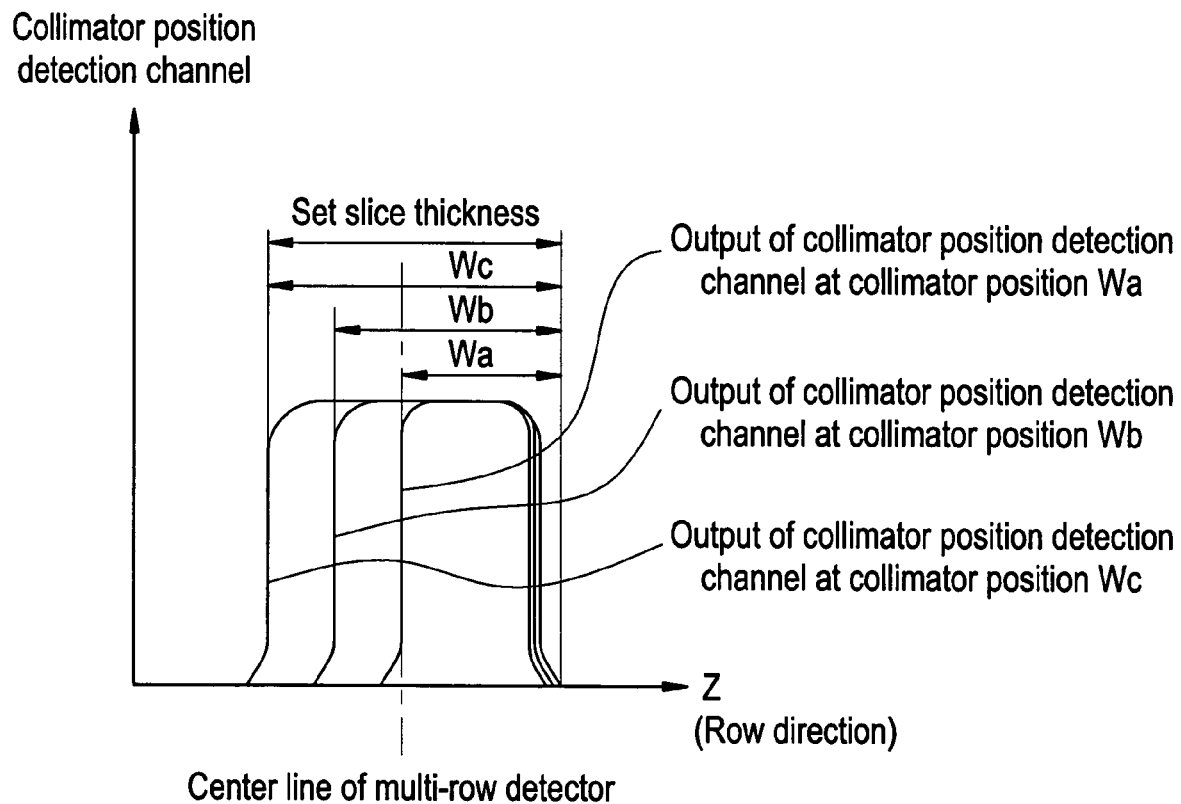
FIG. 16 is a diagram illustrating outputs of collimator position detection channels.
Figure 17:
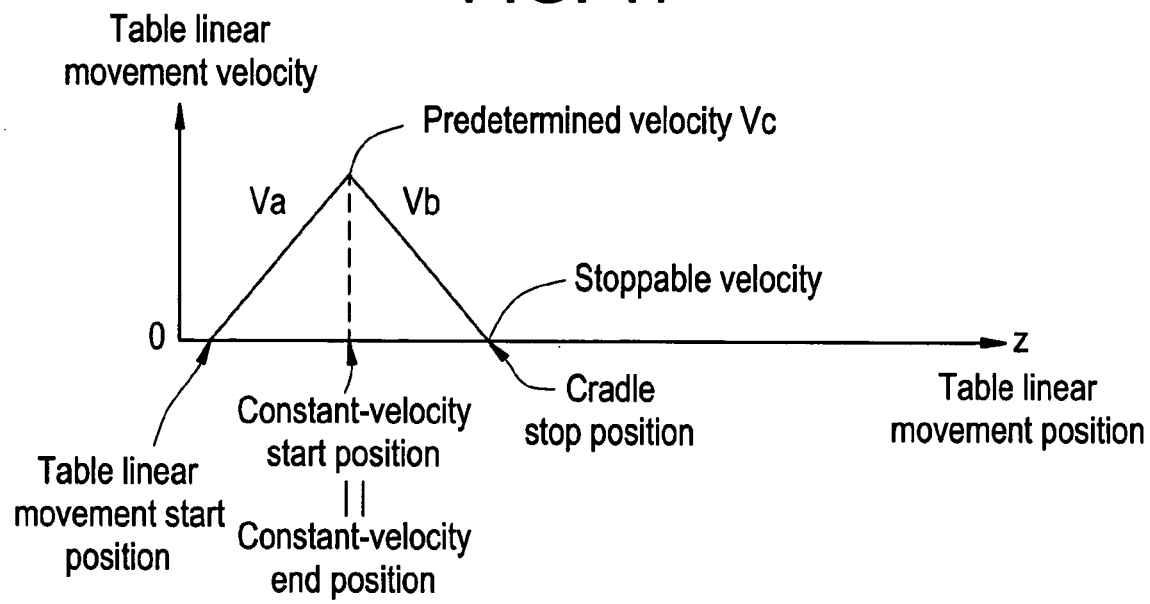
FIG. 17 is a graph illustrating a change in table linear movement velocity where acceleration and deceleration are linearly performed.
Figure 18:
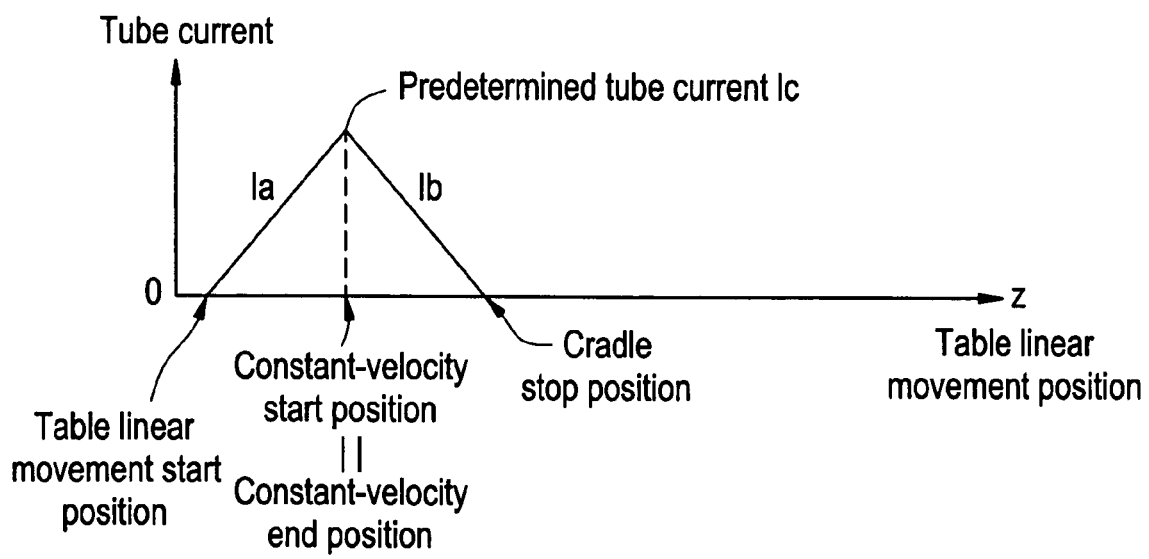
FIG. 18 is a graph depicting a change in tube current where acceleration and deceleration are linearly performed.
Figure 19:
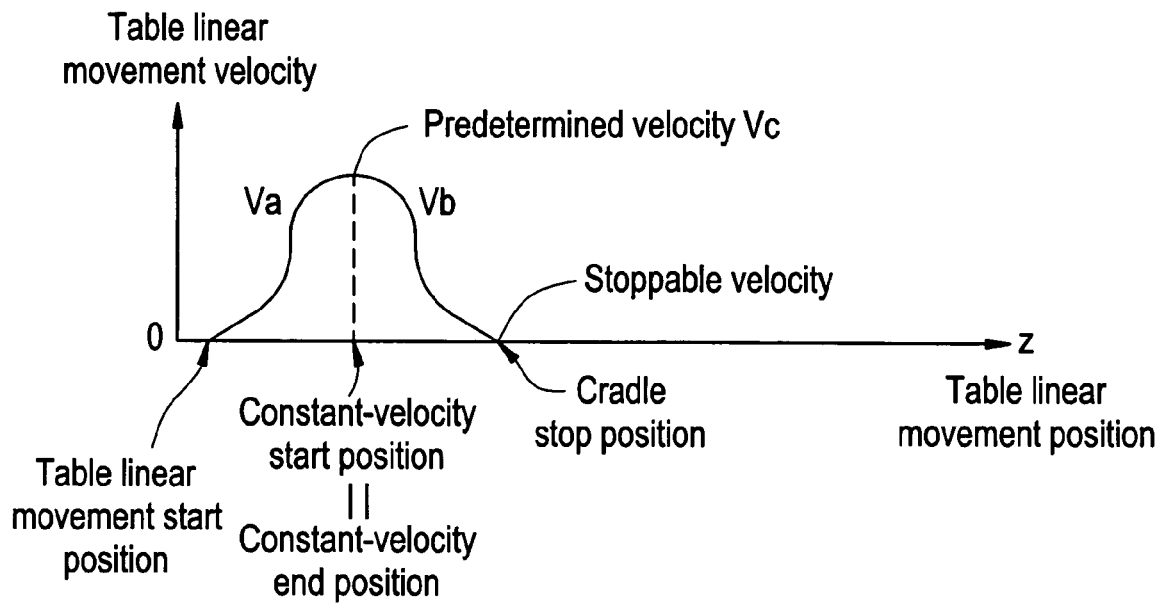
FIG. 19 is a graph showing a change in table linear movement velocity where acceleration and deceleration are nonlinearly performed.
Figure 20:
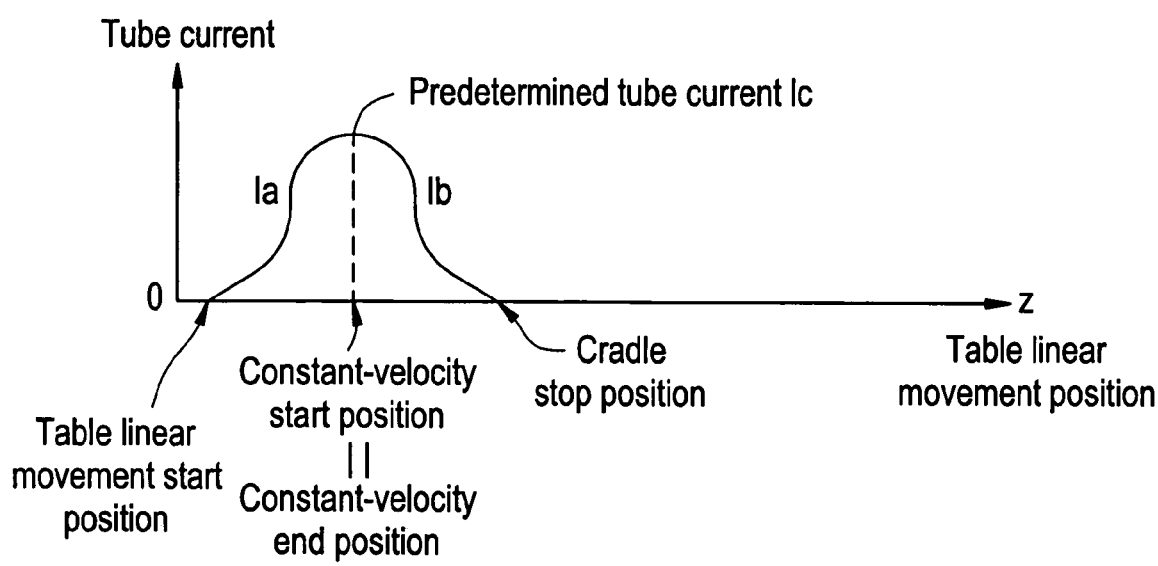
FIG. 20 is a graph depicting a change in tube current where acceleration and deceleration are nonlinearly performed.

The degree of opening/closing of the collimator is measured using each of collimator position detection channels (each corresponding to a diagonally-shaded portion) shown in FIG. 15. When the outputs of the corresponding channels are taken along the z direction (row direction), they are represented as shown in FIG. 16. The degree of opening/closing of the collimator can be recognized by determining widths wa, wb and wc with which detector output signals at this time are outputted. That is, each of the z-direction coordinates counted by the encoder for determining the z-direction coordinates of the photographing table 10 is calculated as a z-axis coordinate by the controller 29, which in turn reaches the DAS 25 through the slip ring 28.

The DAS 25 is capable of recognizing the present degree of opening/closing of the collimator from each of the outputs of the collimator position detection channels. A command can be issued to the collimator 23 in such a manner that the collimator is opened or closed to a collimator opening/closing target value determined from each of the z coordinates.

The difference between a collimator opening/closing value determined from each of the outputs of the collimator position detection channels and the collimator opening/closing target value is determined to generate a feedback signal, and a command is issued to the collimator thereby performing feedback control.

In Step S405, the collimator is kept open only at a location where when $z \geqq 0$. That is, the collimator is controlled in such a manner that zcs=zs=0 is reached.

In Step S406, projection data D0 (view, j, i) in acceleration is acquired.

In Step S407, when the table linear movement velocity of the cradle 12 reaches a predetermined velocity Vc shown in each of FIGS. 11 and 13, the X-ray CT apparatus 100 proceeds to Step 408. When it is determined that the cradle 12 does not reach the predetermined velocity Vc, the X-ray CT apparatus 100 is returned to Step S404, where the table linear movement velocity is further accelerated.

In Step S408, projection data D0 (view, j, i) at low velocity is acquired in a state in which the table linear movement velocity of the cradle 12 is being maintained at a predetermined velocity.

In Step S409, when the cradle 12 has reached the constant-velocity end position shown in each of FIGS. 11 and 13, the X-ray CT apparatus 100 proceeds to Step 410. When it is determined that the cradle 12 does not reach the constant-velocity end position, the X-ray CT apparatus 100 is returned to Step S408, where the acquisition of projection data at constant velocity is continued.

In Step S410, the table linear movement velocity of the cradle 12 is decelerated based on a predetermined function and a tube current is reduced correspondingly. A case in which the predetermined function is linear, is shown in FIGS. 11 and 12. A case in which the predetermined function is non-linear, is shown in FIGS. 13 and 14. When the coordinate zce on the maximum value side in the z direction, of the collimator of the X-ray data acquisition system begins to reach the coordinate ze at the stop of the helical scan, the X-ray CT apparatus starts controlling the opening/closing of the collimator such that zce=ze is reached. When the center coordinate of the X-ray data acquisition system reaches zd=ze, the output of X rays is stopped.

In Step S411, the collimator is kept open only at a location where $z \geqq ze$. That is, the collimator is controlled in such a manner that zce=ze is reached.

In Step S412, projection data D0 (view, j, i) placed under deceleration is acquired.

In Step S413, when the table linear movement velocity of the cradle 12 reaches a stoppable velocity shown in each of FIGS. 11 and 13, the X-ray CT apparatus proceeds to Step S414. When the stoppable velocity is not reached, the X-ray CT apparatus returns to Step S410, where the table linear movement velocity is further decelerated.

In Step S414, the table linear movement of the cradle 12 is stopped.

Incidentally, if the constant velocity start position is set to be equal to the constant velocity end position as shown in FIGS. 17 through 20, then the projection data D0 (view, j, i) can be acquired at the shortest table linear movement distance.

Figure 21:
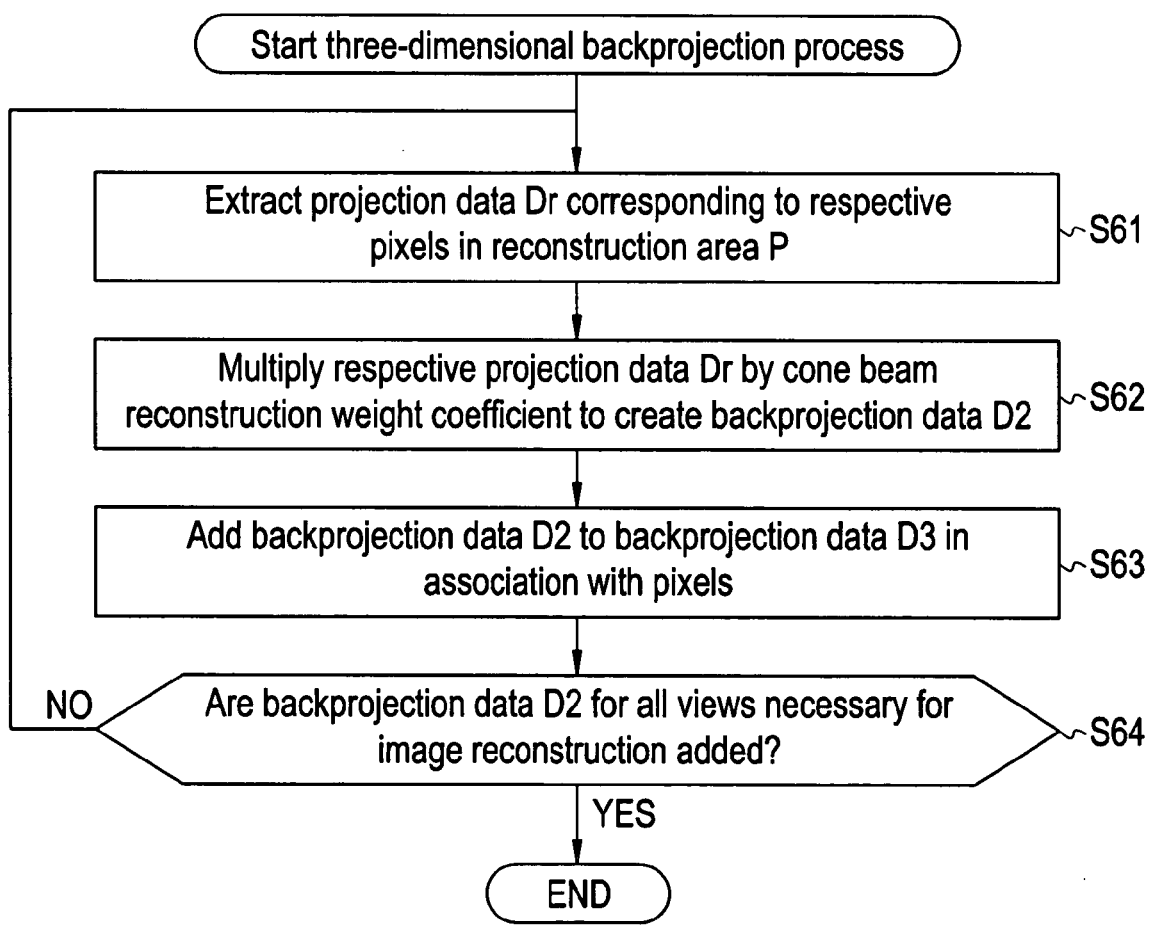
FIG. 21 is a flow diagram illustrating the details of a three-dimensional image reconstructing process.

FIG. 21 is a flow diagram showing the details of the three-dimensional backprojection process (Step S7 in FIG. 3). In Step S61, attention is paid to one of all views (i.e., views corresponding to 360° or views corresponding to "180°+fan angles") necessary for reconstruction of a CT image. Projection data Dr corresponding to respective pixels in a reconstruction area P are extracted.

Figure 22A:
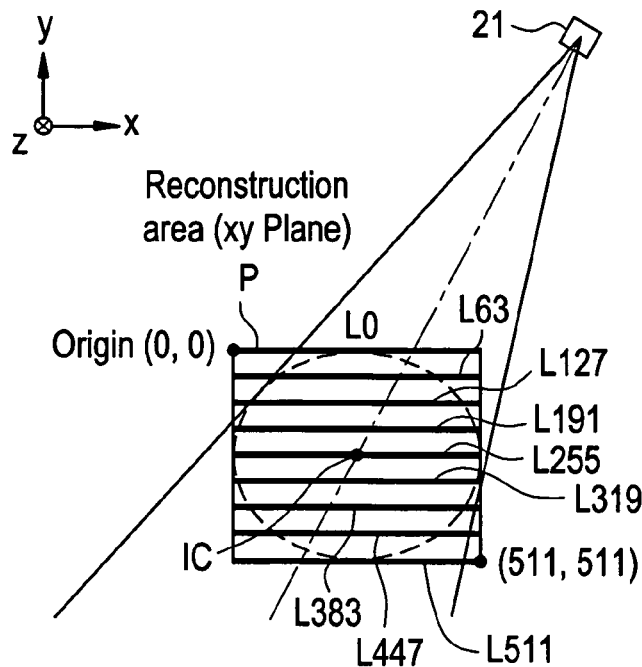
FIGS. 22a and 22b are conceptual diagrams showing a state in which lines on a reconstruction area are projected in an X-ray penetration direction.
Figure 22B:
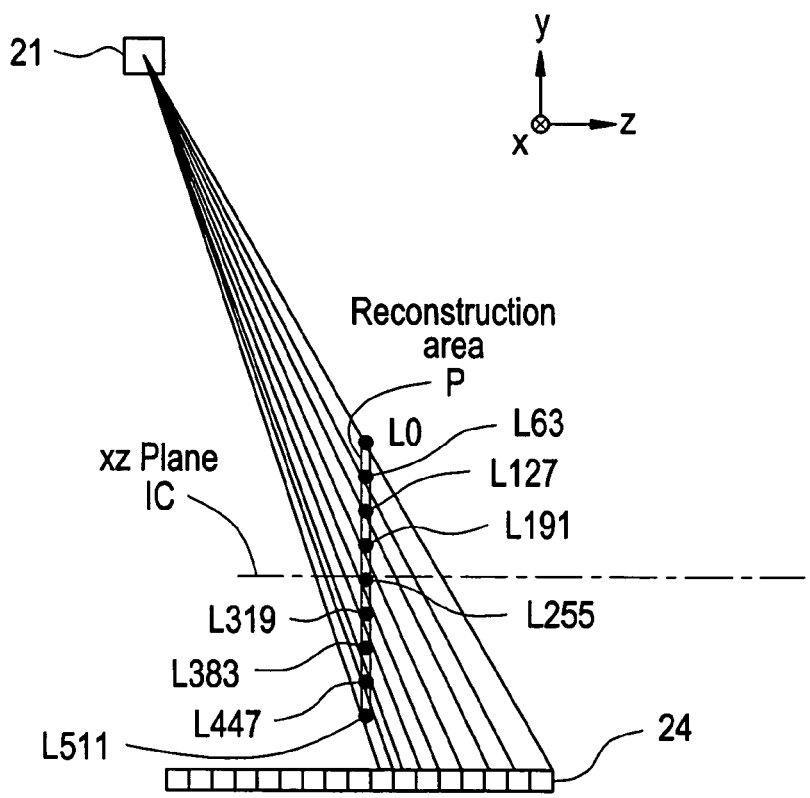
Figure 23:
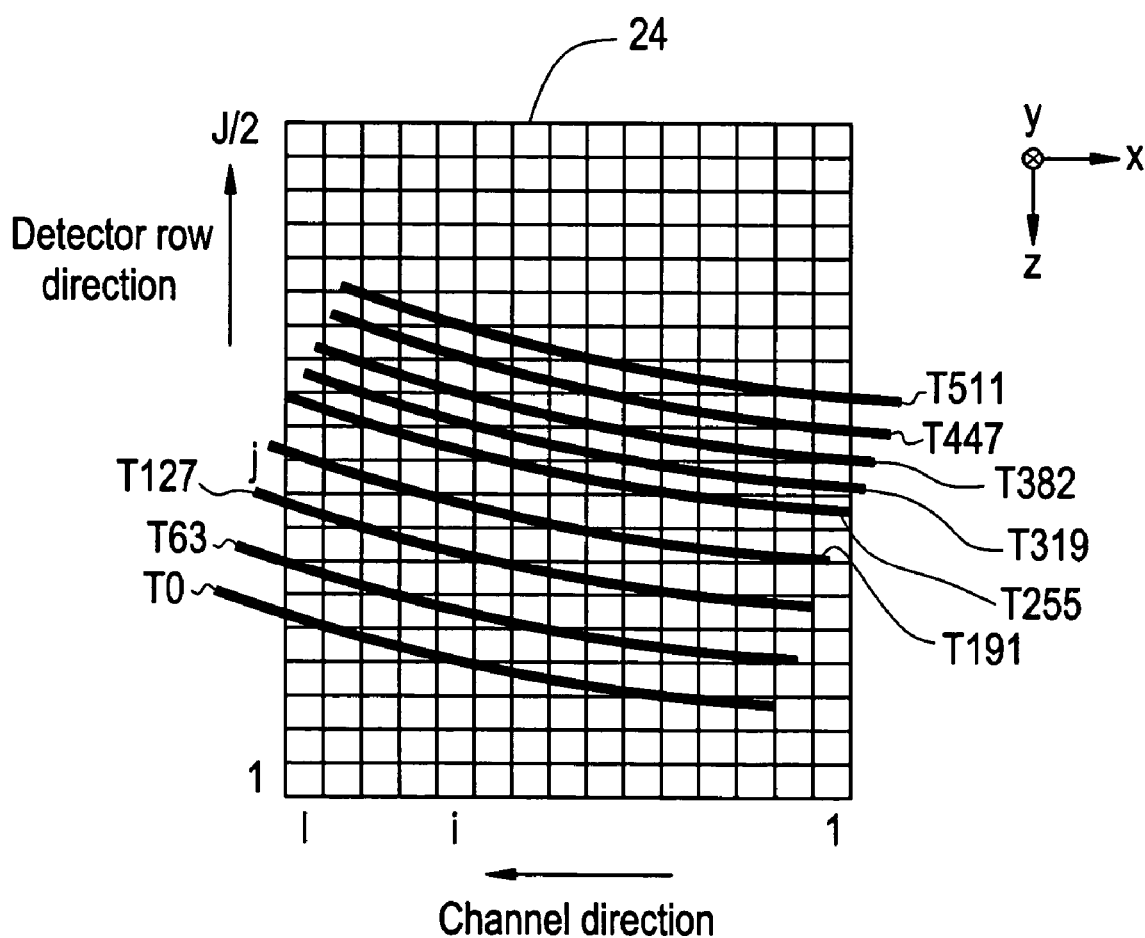
FIG. 23 is a conceptual diagram depicting lines projected on a detector plane.

As shown in FIG. 22, a square area of 512×512 pixels, which is parallel to an xy plane, is defined as a reconstruction area P, and a pixel row L0 parallel to an x axis of y=0, a pixel row L63 of y=63, a pixel row L127 of y=127, a pixel row L191 of y=191, a pixel row L255 of y=255, a pixel row L319 of y=319, a pixel row L383 of y=383, a pixel row L447 of y=477, and a pixel row L511 of y=511 are taken as rows respectively. In this case, when projection data on lines T0 through T511 shown in FIG. 23 obtained by projecting these pixel rows L0 through L511 on the plane of the multi-row X-ray detector 24 in an X-ray penetration direction are extracted in such a condition, then they result in projection data Dr for the pixel rows L0 through L511.

The X-ray penetration direction is determined depending on geometrical positions of an X-ray focal point of the X-ray tube 21, the respective pixels and the multi-row X-ray detector 24. Since, however, the z coordinates of projection data D0 (z, view, j, i) are known, the X-ray penetration direction can be accurately determined even in the case of the projection data (z, view, j, i) placed under acceleration and deceleration.

Incidentally, when some of lines are placed out of the plane of the multi-row X-ray detector 24 as in the case of, for example, the line T0 obtained by projecting the pixel row L0 on the plane of the multi-row X-ray detector 24 in the X-ray penetration direction, the corresponding projection data Dr is set to "0".

Figure 24:
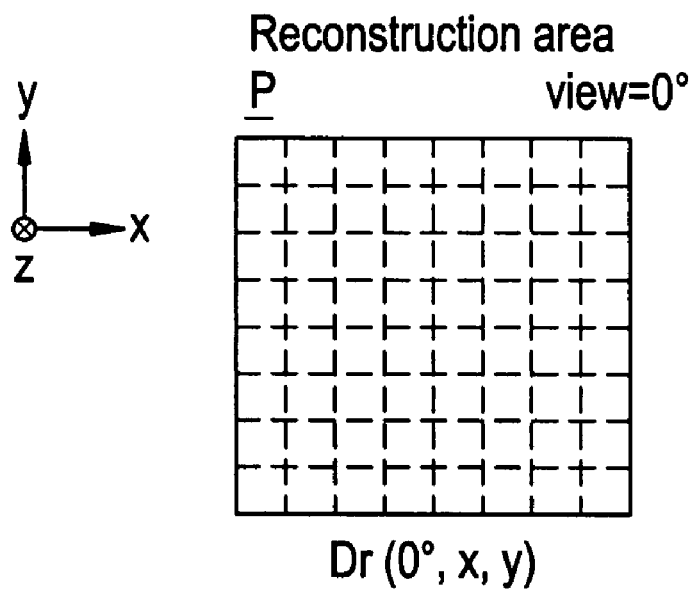
FIG. 24 is a conceptual diagram illustrating a state in which projection data Dr (view, x, y) are projected on a reconstruction area.

Thus, as shown in FIG. 24, the projection data Dr (view, x, y) corresponding to the respective pixels of the reconstruction area P can be extracted.

Figure 25:
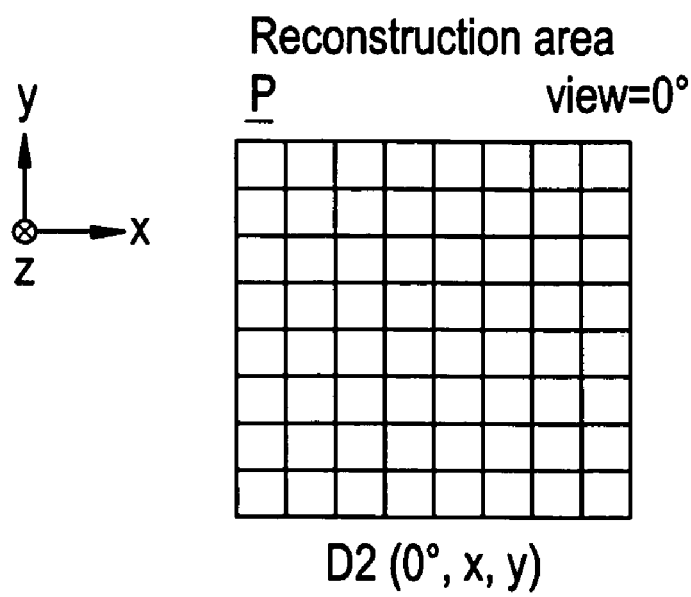
FIG. 25 is a conceptual diagram showing backprojection pixel data D2 of respective pixels on a reconstruction area.

Referring back to FIG. 21, in Step S62, the projection data Dr (view, x, y) are multiplied by a cone beam reconstruction weight coefficient to create projection data D2 (view, x, y) shown in FIG. 25.

When the distance between the focal point of the X-ray tube 21 and each of a detector row j of the multi-row detector 24, corresponding to the projection data Dr and a channel i thereof is assumed to be r0, and the distance between the focal point of the X-ray tube 21 and each of the pixels on the reconstruction area P corresponding to the projection data Dr is assumed to be r1 here, the cone beam reconstruction weight coefficient becomes $(r1/r0)^2$.

Figure 26:
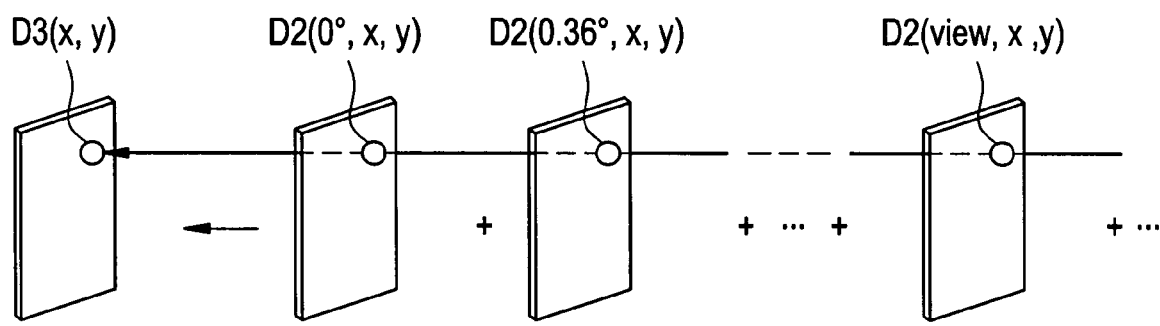
FIG. 26 is an explanatory diagram illustrating a state in which backprojection pixel data D2 are added corresponding to pixels over all views to obtain backprojection data D3.

In Step S63, as shown in FIG. 26, the projection data D2 (view, x, y) are added to the backprojection data D3 (x, y) cleared in advance, in association with pixels.

In Step S64, Steps S61 through S63 are repeatedly effected on all views (i.e., views of 360° or views of "180°+fan angles") necessary for reconstruction of a CT image to obtain backprojection data D3(x, y) as shown in FIG. 26.

Figure 27A:
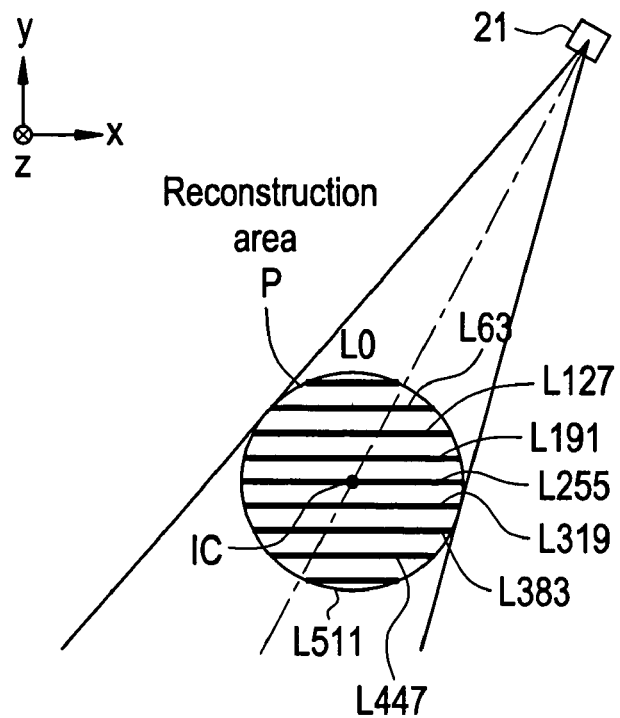
FIGS. 27a and 27b are conceptual diagrams showing a state in which lines on a circular reconstruction area are projected in an X-ray penetration direction.
Figure 27B:
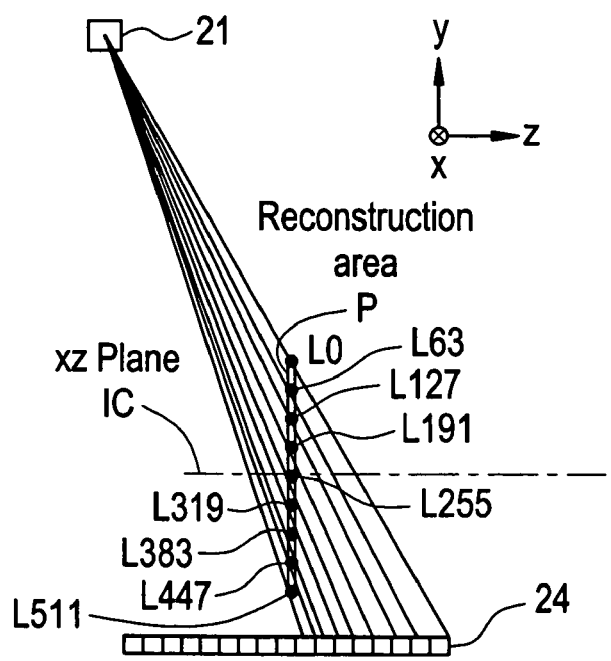

Incidentally, the reconstruction area P may be configured as a circular area as shown in FIG. 27.

According to the X-ray CT apparatus 100 described above, projections data are acquired or collected even during not only a period in which a table linear movement velocity is being kept constant but also a period in which a table linear movement is being under acceleration/deceleration. Coordinate information in a body-axis direction (hereinafter called z axis) while the scan is running, is added to each view data or several view data once. The acquired projection data are used for image reconstruction together with z-axis coordinates and information. Therefore, a table linear moving distance for acceleration/deceleration, of the entire table linear moving distance is also available for image reconstruction.

Incidentally, the three-dimensional image reconstructing method may be a three-dimensional image reconstructing method based on the FeldKamp method known to date. Further, three-dimensional image reconstructing methods proposed by Japanese Patent Application Nos. 2002-066420, 2002-147061, 2002-147231, 2002-235561, 2002-235662, 2002-267833, 2002-322756 and 2002-338947 may be used. A similar effect can be brought about even in the conventional two-dimensional image reconstruction other than the three-dimensional image reconstruction.

Incidentally, although the shutter modes are used at the start and stop of the variable pitch helical in the present embodiment, a similar effect can be brought about even though they are not used.

Although the present embodiment shows the example in which the time intervals and z-direction intervals for image reconstruction of the tomograms during the variable bit helical are constant, they don not always need to be constant even on a time basis and spatially.

Figure 28A:
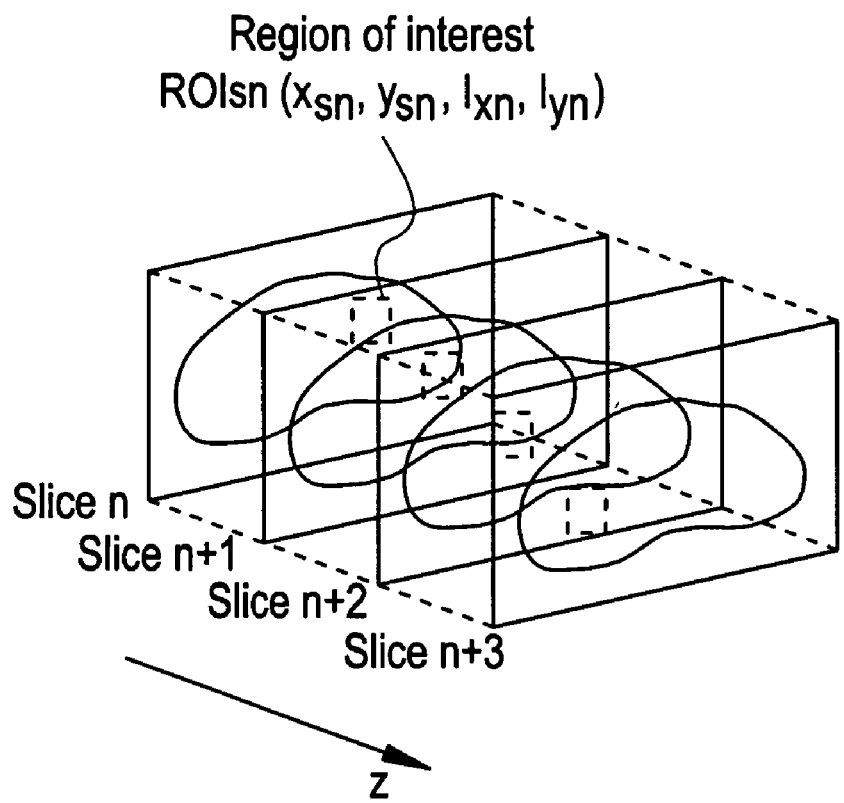
FIGS. 28a and 28b are explanatory diagrams of an example in which regions of interest ROIs for scan phase change every z coordinates.
Figure 28B:
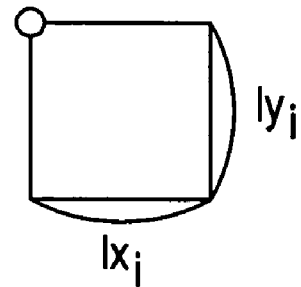

Although the regions of interest ROIs for the scan phase have been described so as to be placed in the same positions as viewed in the z direction in the present embodiment, the positions (xsi, ysi) of regions of interest ROIsi and sizes (Ixi, Iyi) thereof may be changed in the z direction along a blood vessel to be noted as shown in FIG. 28.

Referring back to FIG. 3, in S9, a tomogram is displayed. In S10, a determination whether a scan has ended is made. Upon determining that a scan has ended, the scan-control method ends. On the other hand, upon determining that a scan has not ended, in S11, a plurality of CT values in a plurality of regions of interest of a plurality of sheets of reconstruction tomograms are measured. In S12, a determination is made whether all the CT values of the regions of interest of the plurality of sheets of reconstruction tomograms exceed a predetermined value. Upon determining that the CT values of the regions of interest exceed the predetermined value, the scan-control method returns to S4. On the other hand, upon determining that the CT values of the regions of interest of the plurality of sheets do not exceed the predetermined value, in S13, a velocity of bloodstream is measured and a velocity of helical scan is decelerated.

Figure 29:
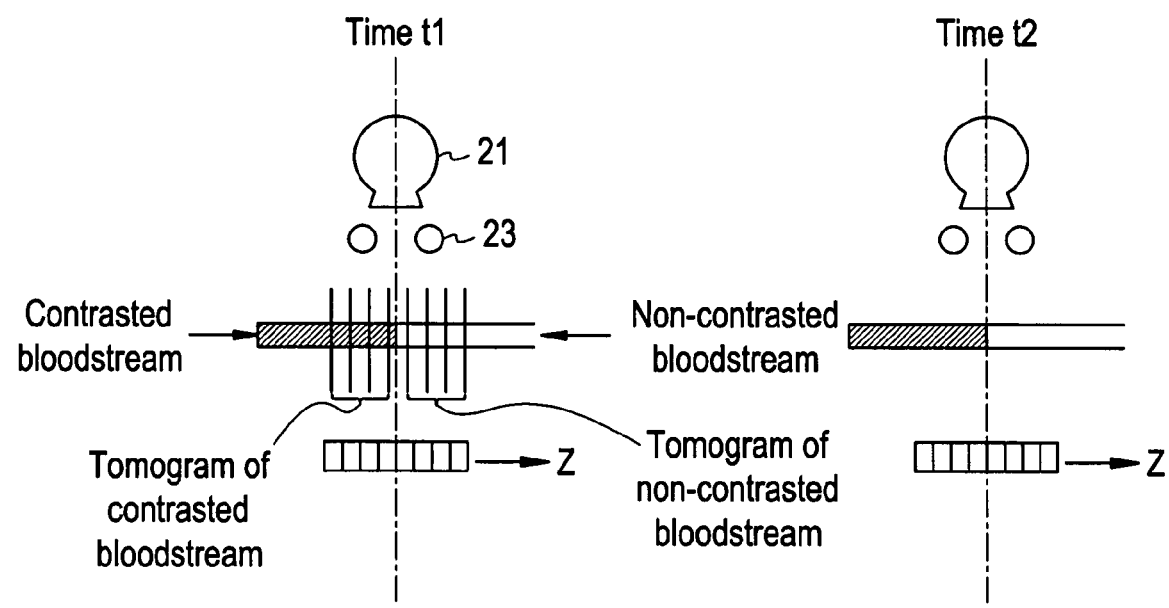
FIG. 29 is an explanatory diagram of an example in which the most leading edge of a contrasted bloodstream is controlled so as to be always placed in the center of a data acquisition system as viewed in a z direction in an embodiment 2.

Next, FIGS. 29 and 30 show an embodiment 2. In this case, the accuracy of tracking of the most leading edge of each bloodstream contrasted in the embodiment is improved, and the center coordinate of a data acquisition system in a z direction is always controlled so as to go to approach the neighborhood of the most leading edge of each contrasted bloodstream.

FIG. 29 is an explanatory diagram showing an example in which the most leading edge of each contrasted bloodstream is controlled so as to be always placed in the center of the data acquisition system as viewed in the z direction in the embodiment 2. FIG. 30 shows the manner in which only a contrasted bloodstream is extracted from images corresponding to differences, at the same regions and locations, among tomograms of contrasted bloodstreams and tomograms of non-contrasted bloodstreams in the embodiment 2. By performing one variable pitch helical scan in this way, only the contrasted bloodstream is extracted, so that it can be brought into image form.

Many widely different embodiments of the invention may be configured without departing from the spirit and the scope of the present invention. It should be understood that the present invention is not limited to the specific embodiments described in the specification, except as defined in the appended claims.

The invention claimed is:

1. A scan control method for an X-ray CT apparatus wherein a subject with a contrast agent injected therein is helically scanned with an X-ray beam and image reconstruction is performed based on projection data obtained through an X-ray detector, said method comprising:

changing, at a slice position, a first non-zero velocity of a helical scan to a second velocity based on a moving velocity, at the slice position, of the contrast agent in the subject, wherein the moving velocity is determined using a position, relative to a center point of the X-ray detector, of a tomogram of a leading edge of the contrast agent, wherein the tomogram is identified from a plurality of tomograms based on a threshold CT number.

2. The scan control method according to claim 1, wherein the X-ray detector is a multi-row X-ray detector, a matrix-form X-ray detector, or a plane matrix-form X-ray detector.

3. The scan control method according to claim 1, wherein each of the plurality of tomograms are reconstructed by a three-dimensional backprojection process and are different in position as viewed in the direction of progress of the helical scan.

4. The scan control method according to claim 3, wherein intervals among the plurality of tomograms as viewed in the progress direction of the helical scan are constant.

5. The scan control method according to claim 3, wherein intervals among the plurality of tomograms as viewed in the progress direction of the helical scan are indefinite intervals.

6. The scan control method according to claim 1, wherein the tomogram, at which the head of the contrast agent has arrived, is detected based on a CT value of a predetermined region of interest in each of the plurality of tomograms.

7. The scan control method according to claim 6, wherein the regions of interest are set independently for every individual tomogram of the plurality of tomograms.

8. The scan control method according to claim 6, wherein a monitoring scan for detecting a change in the CT value of each of the regions of interest is performed prior to the start of the helical scan.

9. The scan control method according to claim 1, wherein the first velocity of the helical scan is changed continuously halfway through the scan.

10. The scan control method according to claim 1, wherein the helical scan is controlled in such a manner that the position of center of the X-ray detector as viewed in the progress direction of the helical scan is equivalent to the position of a leading end of the contrast agent, and wherein images are reconstructed on the basis of projection data respectively obtained through a first half of the X-ray detector and a latter half of the X-ray detector as viewed in the progress direction of the helical scan with respect to the center position of the X-ray detector and thereby an image corresponding to a difference between the images is obtained.

11. An X-ray CT apparatus comprising:
an X-ray source;
an X-ray detector disposed so as to be opposed to the X-ray source with a subject with a contrast agent injected therein being interposed therebetween;
an image reconstructing device for helically scanning the subject and reconstructing an image on the basis of projection data obtained through the X-ray detector; and
a control device for controlling a helical scan, wherein the control device is configured to change, at a slice position, a first non-zero scan velocity of the helical scan to a second velocity based on a moving velocity, at the slice position, of the contrast agent in the subject, wherein the moving velocity is determined using a position, relative to a center point of the X-ray detector, of a tomogram of a leading edge of the contrast agent, wherein the tomogram is identified from a plurality of tomograms based on a threshold CT number.

12. The X-ray CT apparatus according to claim 11, wherein the X-ray detector is a multi-row X-ray detector, a matrix-form X-ray detector, or a plane matrix-form X-ray detector.

13. The X-ray CT apparatus according to claim 11, wherein the control device is configured to determine the moving velocity of the contrast agent based on a plurality of tomograms reconstructed by a three-dimensional backprojection process and different in position as viewed in the direction of progress of the helical scan.

14. The X-ray CT apparatus according to claim 13, wherein intervals among the plurality of tomograms as viewed in the progress direction of the helical scan are constant.

15. The X-ray CT apparatus according to claim 13, wherein intervals among the plurality of tomograms as viewed in the progress direction of the helical scan are indefinite intervals.

16. The X-ray CT apparatus according to claim 11, wherein the control device is configured to identify the tomogram, at which the head of the contrast agent has arrived, based on a CT value of a predetermined region of interest in each of the plurality of tomograms.

17. The X-ray CT apparatus according to claim 16, wherein the regions of interest are set independently for every individual tomogram of the plurality of tomograms.

18. The X-ray CT apparatus according to claim 16, wherein the control device is configured to perform a monitoring scan for detecting a change in the CT value of each of the regions of interest prior to the start of the helical scan.

19. The X-ray CT apparatus according to claim 11, wherein the control device is configured to change the first velocity of the helical scan continuously halfway through the scan.

20. The X-ray CT apparatus according to claim 11, wherein the X-ray detector is a multi-row X-ray detector or a plane X-ray detector, wherein the control device is configured to control the helical scan in such a manner that the position of center of the X-ray detector as viewed in the progress direction of the helical scan is equivalent to the position of a leading end of the contrast agent, and wherein the image reconstructing device reconstructs images on the basis of projection data respectively obtained through a first half of the X-ray detector and a latter half of the X-ray detector as viewed in the progress direction of the helical scan with respect to the center position of the X-ray detector and thereby obtains an image corresponding to a difference between the images.

* * * * *